United States Patent
Steinmetz et al.

(10) Patent No.: US 10,232,057 B2
(45) Date of Patent: Mar. 19, 2019

(54) TARGETING CANCER CELLS AND TISSUE USING FILAMENTOUS PLANT VIRUS PARTICLES

(71) Applicant: CASE WESTERN RESERVE UNIVERSITY, Cleveland, OH (US)

(72) Inventors: Nicole F. Steinmetz, Cleveland Heights, OH (US); Sourabh Skukla, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 213 days.

(21) Appl. No.: 15/306,786

(22) PCT Filed: May 31, 2013

(86) PCT No.: PCT/US2013/043650
§ 371 (c)(1),
(2) Date: Oct. 26, 2016

(87) PCT Pub. No.: WO2013/181557
PCT Pub. Date: Dec. 5, 2013

(65) Prior Publication Data
US 2017/0106098 A1    Apr. 20, 2017

Related U.S. Application Data

(60) Provisional application No. 61/653,828, filed on May 31, 2012.

(51) Int. Cl.
A61K 47/60    (2017.01)
A61K 49/00    (2006.01)
A61K 47/69    (2017.01)

(52) U.S. Cl.
CPC .......... *A61K 49/005* (2013.01); *A61K 47/60* (2017.08); *A61K 47/6901* (2017.08); *A61K 49/0002* (2013.01); *A61K 49/0021* (2013.01); *A61K 49/0097* (2013.01)

(58) Field of Classification Search
None
See application file for complete search history.

(56) References Cited

PUBLICATIONS

Santa Cruz et al. Assembly and movement of a plant virus carrying a green fluorescent protein overcoat. Proc. Natl. Acad. Sci. USA. vol. 93, pp. 6286-6290, Jun. 1996.*
Steinmetz et al. Potato Virus X as a Novel Platform for Potential Biomedical Applications. Nano Lett. 2010, 10, 305-312.*
Brunel et al. Hydrazone ligation strategy to assemble multifunctional viral nanoparticles for cell imaging and tumor targeting. Nano Lett. Mar. 10, 2010;10(3):1093-7.*
Steinmetz et al. PEGylated Viral Nanoparticles (VNPs) for Biomedicine: the Impact of PEG Chain Length on VNP cell interactions in vitro and ex vivo. Biomacromolecules. Apr. 13, 2009; 10(4): 784-792.*

* cited by examiner

*Primary Examiner* — Nianxiang Zou
(74) *Attorney, Agent, or Firm* — Tarolli, Sundheim, Covell & Tummino LLP

(57) ABSTRACT

A filamentous plant virus carrier comprising a filamentous plant virus particle that has been modified to carry an imaging agent or cytotoxic compound is described. The filamentous plant virus carrier can be used in a method of targeting cancer cells and tissue by administering it to a subject. Cancer tissue targeted by the filamentous plant virus carrier can be imaged using an imaging agent, or treated using a cytotoxic compound.

16 Claims, 8 Drawing Sheets

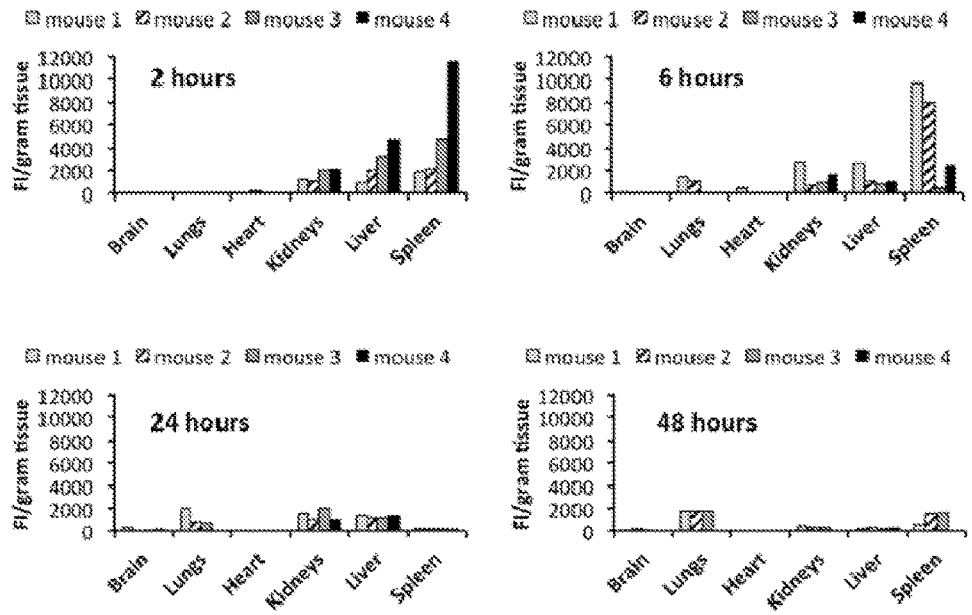
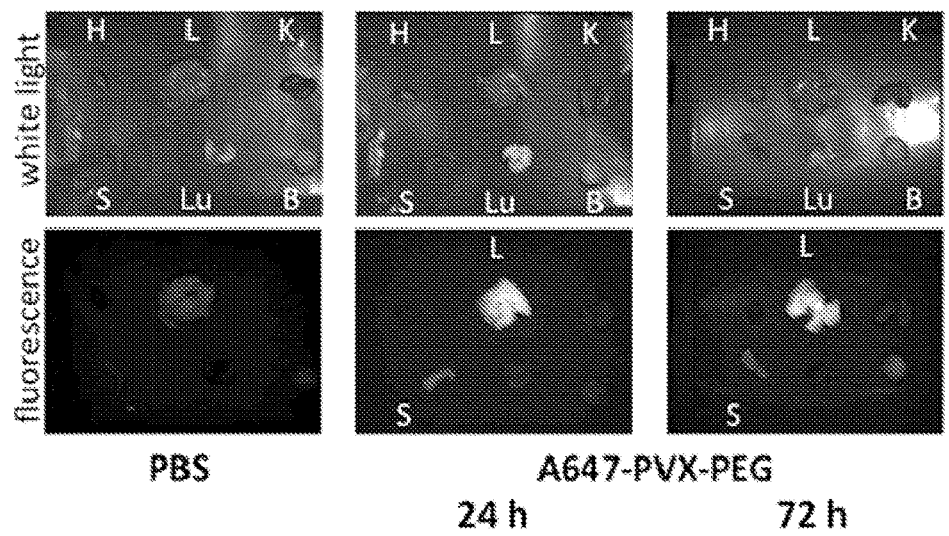
Figs. 6A-B

TARGETING CANCER CELLS AND TISSUE USING FILAMENTOUS PLANT VIRUS PARTICLES

RELATED APPLICATION

This application claims priority from U.S. Provisional Application No. 61/653,828, filed May 31, 2013, the subject matter of which is incorporated herein by reference in its entirety.

GOVERNMENT FUNDING

This invention was made with government support under Grant No. EB011317 awarded by The National Institutes of Health. The United States government has certain rights in the invention.

BACKGROUND

The ability of nanoparticles to carry large drug payloads and the ease with which ligands can be added so that the payload is delivered to specific target sites (e.g. cancer or cardiovascular disease) make them particularly promising for biomedical applications. The chemical composition and physical properties of nanomaterials such as shape and elasticity can significantly impact their fates in vivo. Recent studies indicate that filamentous nanomaterials have superior pharmacokinetic and tumor-homing properties. Decuzzi et al., Journal of Controlled Release 141, 320-327 (2010).

Several viral nanoparticles (VNPs) are currently being developed for nanomedical applications, where the vast majority of platforms under investigation are of spherical nature, e.g. the Human papilloma virus (HPV)-based Gardasil vaccine, Adenovirus-based gene-delivery vectors, and various plant viruses including Cowpea mosaic virus (CPMV), Brome mosaic virus (BMV), Cowpea chlorotic mottle virus (CCMV), Hibiscus chlorotic ringspot virus (HCSRV), and Red clover necrotic mottle virus (RCNMV). In contrast, few high aspect ratio VNPs have been investigated. Those that have, including Tobacco mosaic virus and bacteriophage M13, have focused mainly on in vitro tissue engineering applications. Pokorski, J. K. and N. F. Steinmetz. Mol Pharm 8(1): 29-43 (2011).

Still, the vast majority of platform technologies currently under development consist of spherical or elongated low aspect ratio materials (AR<5). While carbon-based nanotubes and filomicelles are notable exceptions, carbon nanotubes have low biocompatibility (Firme et al., Nanomedicine: nanotechnology, biology, and medicine 6, 245-256 (2010)) and filomicelles are in the micron-size regime. Geng et al., Nat Nanotechnol 2, 249-255 (2007). Physically and chemically tailoring materials at the nanoscale in two dimensions to create high aspect ratio materials is challenging using synthetic materials, mainly due to polydispersity and poorly controlled chemistry. Efforts in synthetic chemistry and nanotechnology have sought to mimic characteristics such as self-assembly and programmability at the atomic level that nature has already achieved. Therefore, a bio-inspired approach to engineer viral nanoparticles (VNPs) from plants for imaging and drug delivery is desirable.

SUMMARY

Nanomaterials with elongated architectures have been shown to possess differential tumor homing properties compared to their spherical counterparts. Potato virus X (PVX) and Cowpea mosaic virus (CPMV) show distinct biodistribution profiles and differ in their tumor homing and penetration efficiency. Analogous to what is seen with inorganic nanomaterials, PVX shows enhanced tumor homing and tissue penetration. Human tumor xenografts exhibit higher uptake of PEGylated filamentous PVX compared to CPMV, particularly in the core of the tumor. This is supported by immunohistochemical analysis of the tumor sections, which indicates greater penetration and accumulation of PVX within the tumor tissues. The enhanced tumor homing and retention properties of PVX along with its higher payload carrying capacity makes it a potentially superior platform for applications in cancer drug delivery and imaging applications.

The filamentous plant virus Potato virus X was recently introduced by the inventors as a new platform presenting a unique nanoarchitecture difficult to be synthesized chemically. Herein, a detailed analysis of PVX biodistribution and clearance in healthy mice and mouse tumor xenograft models is presented using a combination of ex vivo whole-organ imaging, quantitative fluorescence assays and immunofluorescence microscopy. While up to 30% of the injected dose of PVX nanoparticles homed to the colon, mammary, brain, fibrosarcoma, and squamous carcinoma tumor xenografts, remaining particles were cleared initially by the reticuloendothelial system organs spleen and liver followed by slower processing and clearance through the kidneys and bile.

In one aspect, a filamentous plant virus carrier, comprising a filamentous plant virus particle that has been modified to carry an imaging or antitumor agent is provided. In some embodiments, the filamentous plant virus belongs to the Alphaflexiviridae family, while in further embodiments the filamentous plant virus belongs to the Potato virus X species. In further embodiments, the filamentous plant virus carrier is PEGylated to reduce immunogenicity. In additional embodiments, PEGylation is also used to enhance stability and pharmacokinetics.

Another aspect of the invention provides a method of targeting cancer tissue in a subject, by administering to the subject a filamentous plant virus carrier comprising a filamentous plant virus particle modified to carry an imaging agent or a cytotoxic compound such as an antitumor agent. In some embodiments, the filamentous plant virus belongs to the Alphaflexiviridae family, while in further embodiments the filamentous plant virus belongs to the Potato virus X species. In some embodiments, the cancer tissue is colon cancer, brain cancer, or breast cancer, fibrosarcoma, and squamous carcinoma. In further embodiments, the filamentous plant virus carrier is administered together with a pharmaceutically acceptable carrier.

BRIEF DESCRIPTION OF THE FIGURES

The present invention may be more readily understood by reference to the following drawings.

FIG. 6 provides graphs and images showing the biodistribution of A647-PVX-PEG in Balb/c mice. A) Fluorescence intensity (of A647-PVX-PEG) per gram tissue weights (FI/g) at 2 h, 6 h, 24 h and 48 h post-administration of A647-PVX-PEG (intravenously via tail vein of Balb/c animals) measured based on fluorescence intensity; B) Ex vivo Maestro imaging of tissues harvested from Balb/c mice injected with PBS (t=24 hrs) and A647-PVX-PEG (t=24 hrs and 72 hrs) post-administration.

Figure 1:
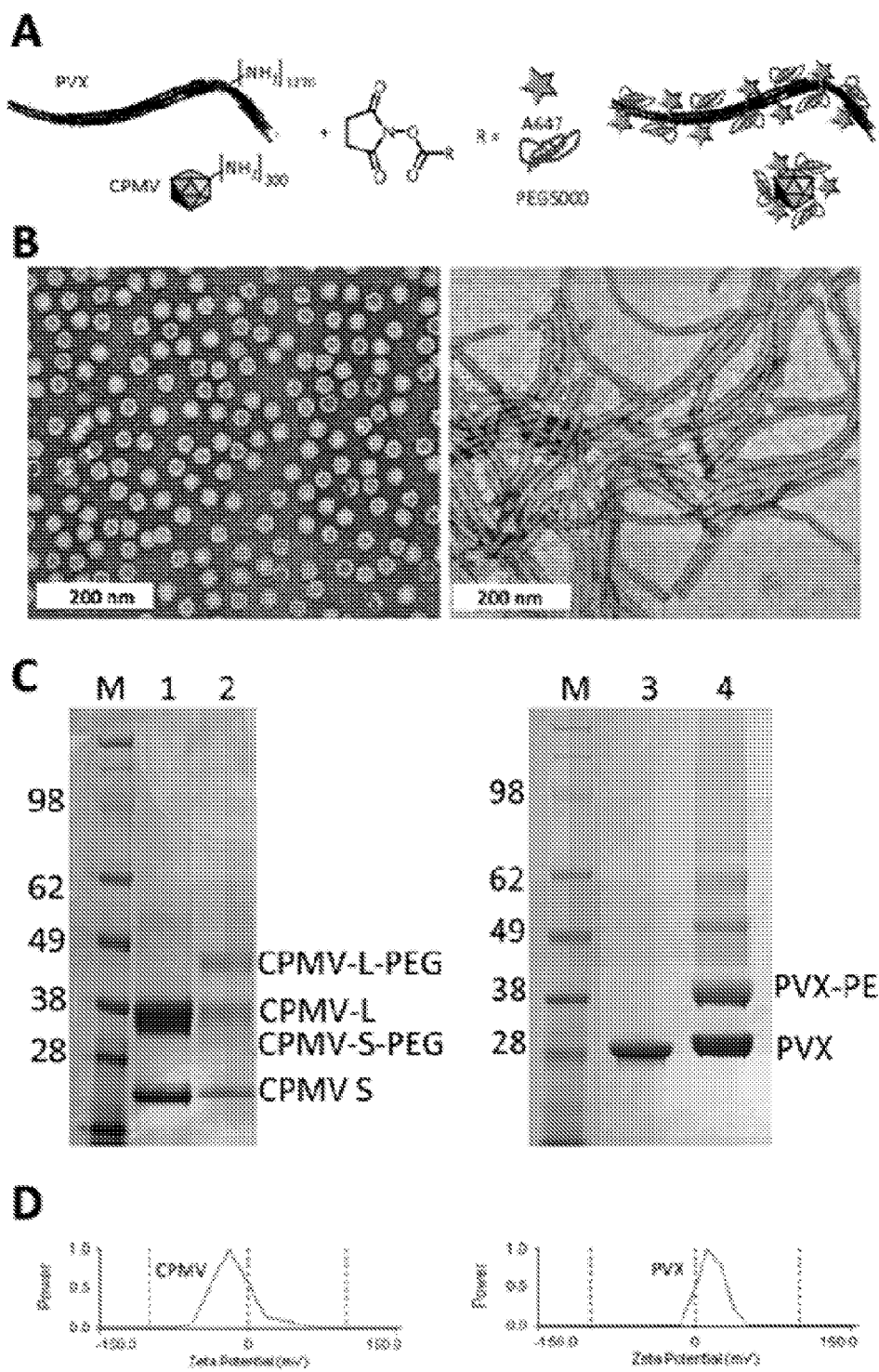
FIG. 1 provides A) a bioconjugation scheme showing A647 and PEG5000 conjugation to solvent-exposed Lys side chains on PVX and CPMV; B) a TEM of negatively-stained (2% w/v UAc) A647-CPMV-PEG (left) and A647-PVX-PEG5000 (right); C) an SDS gel after Coomassie staining of separated coat proteins. M=SeeBluePlus 2 protein marker, numbers indicate molecular weight standards in kDa. 1=CPMV, 2=A647-CPMV-PEG, 3=PVX, and 4=A647-PVX-PEG5000. CPMV consists of S and L protein, PVX consists of a single coat protein. Lower mobility bands indicate PEGylation. Band density analysis was performed using band analysis tool and ImageJ software; and D) a graph showing the zeta potential of A647-labeled and PEGylated VNPs.

FIG. 8 provides graphs and images of Maestro imaging analysis of HT-29, 4T1 and Gli36Δ5 tumor xenografts from animals sacrificed at different time points post i.v. administration of A647-PVX-PEG. A) Maestro images of HT-29 tumors at 24 h, 72 h and 120 h post administration and the confocal images of corresponding tumor sections showing PVX penetration into tumor tissue via the tumor vasculature CD31 (scale bar is 50 μm). B) Representative Maestro images of tissue biodistribution in the HT-29 xenograft mice (n=3) at various time points postinjection and the corresponding relative fluorescence signal intensity measured using Image J. C) Comparative maestro imaging analysis of HT-29, 4T1 and Gli36Δ5 tumor xenografts 24 h post-injection with PBS or A647-PVX-PEG and their corresponding fluorescence intensities analyzed using Image J software (n=3, expect for HT-29 tumors/PBS with n=2, one animal had to be sacrificed).

DETAILED DESCRIPTION

Plant viral nanoparticles and nanofilaments, including the potato virus X, may be used as platforms for diagnostics and therapeutics. VNPs come in many shapes and sizes and some species are truly monodisperse, highly symmetrical and the structure is known to atomic precision. VNPs can be engineered with targeting ligands, drugs and/or imaging molecules. Pokorski, J. K. & Steinmetz, N. F., Mol Pharm 8, 29-43 (2011).

The biodistribution and tumor homing properties of the high aspect ratio, filamentous plant VNP PVX was compared to the 30 nm-sized icosahedral Cowpea mosaic virus (CPMV). CPMV has been extensively studied and developed, and its in vivo properties are well understood. Singh et al., J Control Release 120, 41-50 (2007). It can be regarded as a prototype VNP for in vivo medical applications.

The VNP platforms may be engineered and tailored for desired applications through genetic modification or bioconjugate chemistry. CPMV nanoparticles consist of 60 copies of each a small and large protein and offer 300 reactive Lys side chains per particle (Chatterji et al., Chem Biol 11, 855-863 (2004)), which can be functionalized using N-hydroxysuccinimidyl ester (NHS)-activated probes and linkers. PVX nanofilaments measure 515×13 nm (AR 40), and consist of 1270 identical coat protein units. Essentially all 1270 coat proteins can be chemically addressed via their reactive Lys side chains using NHS chemistry. Steinmetz et al., Nano Lett., 10, 305-12 (2010).

The tumor homing efficiency and biodistribution of PVX and CPMV formulations were evaluated in human fibrosarcoma, squamous carcinoma, and colon cancer xenograft tumors in both chicken chorioallantoic membrane (CAM) and mouse models. PVX was also evaluated in mouse models of brain and breast cancer.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms “a”, “an” and “the” include plural references unless the content clearly dictates otherwise. Thus, for example, reference to “a cell” includes a combination of two or more cells, and the like.

The term “about” as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, or blood.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Targeting," as used herein, refers to the ability of filamentous plant virus particles to be delivered to and preferentially accumulate in cancer tissue in a subject.

In one aspect, the invention provides a method of using a filamentous plant virus to target cancer tissue in a subject. The method includes administering a filamentous plant virus carrier comprising a filamentous plant virus particle modified to carry an imaging agent or a cytotoxic compound to the subject.

Filamentous Plant Viruses

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm Filament-like virus particles are flexible in addition to being long and thin, and therefore some embodiments of the invention are directed to use of a flexible filamentous plant virus. As described herein, use of filamentous plant viruses provides the advantages of improved tumor targeting and penetration. Embodiments of the invention can deliver about 10%, about 20%, about 30%, about 40%, or even about 50% or more of the injected dose to tumor tissue.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

The filamentous plant virus is used to target cancer tissue in a subject. As defined herein, targeting cancer tissue refers to the ability of the filamentous plant virus particles to reach and preferably accumulate within cancer tissue after being administered to the subject. The ability of filamentous plant virus particles to target cancer tissue is supported by the biodistribution studies described herein. While not intending to be bound by theory, it currently appears that filamentous plant virus particles are taken up by blood components such as macrophage cells of the immune system, which subsequently accumulate in tumor tissue, thereby delivering the filamentous plant virus to the tumor cells.

Conjugation of Imaging Agents and Cytotoxic Compounds

The invention makes use of a filamentous plant virus particle that has been modified to carry an imaging agent or a cytotoxic compound. Including an imaging agent or a cytotoxic compound provides the capability for the virus particle to function as a targeted imaging agent or a targeted cytotoxic agent. A filamentous plant virus (i.e., filamentous plant virus particle) that has been modified to include an imaging agent or a cytotoxic compound) is also referred to herein as a filamentous plant virus carrier.

In general, imaging agents and/or cytotoxic compounds (collectively referred to herein as agents) can be conjugated to the filamentous plant virus by any suitable technique, with appropriate consideration of the need for pharmacokinetic stability and reduced overall toxicity to the patient. The term "conjugating" when made in reference to an agent and a filamentous plant virus particle as used herein means covalently linking the agent to the virus subject to the single limitation that the nature and size of the agent and the site at which it is covalently linked to the virus particle do not interfere with the biodistribution of the modified virus.

An agent can be coupled to a filamentous plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the agent or the virus particle, and thus increase the coupling efficiency. A preferred group suitable for attaching agents to the virus particle are lysine residues present in the viral coat protein.

Suitable linkage chemistries include maleimidyl linkers and alkyl halide linkers and succinimidyl (e.g., N-hydroxysuccinimidyl (NHS)) linkers (which react with a primary amine on the filamentous plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, for example where a cytotoxic moiety is more potent when free from the targeting/imaging molecules of the present invention, it can be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

It can be desirable to couple more than one cytotoxic and/or imaging moiety to a filamentous plant virus particle of the invention. By poly-derivatizing the filamentous plant viral particle of the invention, several cytotoxic strategies can be simultaneously implemented. For example, a virus carrier can be made useful as a contrasting agent for several visualization techniques, or a virus carrier including a cytotoxic agent can be labeled for tracking by a visualization technique. In one embodiment, multiple molecules of a cytotoxic compound are coupled to a filamentous plant virus particle. In another embodiment, more than one type of cytotoxic compound can be coupled to a filamentous plant virus particle.

Imaging Agents

In some embodiments, the filamentous plant virus particle is modified to carry an imaging agent; i.e., the plant virus carrier comprises an imaging agent. Examples of imaging agents include fluorescent, radioactive isotopes, MRI contrast agents, enzymatic moieties, or detectable label of the invention. For example, in some embodiments, the imaging agent is a fluorescent molecule for fluorescent imaging. The detectable group can be any material having a detectable physical or chemical property. Such detectable labels have been well-developed in the field of fluorescent imaging, magnetic resonance imaging, positive emission tomography, or immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, AlexaFluor555, Texas red, rhodamine, and the like), radiolabels (e.g., $^3H$, $^{14}C$, $^{35}S$, $^{125}I$, $^{121}I$, $^{112}In$, $^{99}mTc$), other imaging agents such as microbubbles (for ultrasound imaging), $^{18}F$, $^{11}C$, $^{15}O$, (for Positron emission tomography), $^{99}mTC$, $^{111}In$ (for Single photon emission tomography), gadolinium chelate or iron (for magnetic resonance imaging), enzymes (e.g., horse radish peroxidase, alkaline phosphatase and others commonly used in an ELISA), and colorimetric labels such as colloidal gold or colored glass or plastic (e.g. polystyrene, polypropylene, latex, and the like) beads. See also Handbook of Fluorescent Probes and Research Chemicals, $6^{th}$ Ed., Molecular Probes, Inc., Eugene, Oreg., which is incorporated herein by reference.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include compounds of the Alexa Fluor® series (Invitrogen™), fluorescein and its derivatives, rhodamine and its derivatives, dansyl, umbelliferone, and the like Chemiluminescent compounds include luciferin, and 2,3-dihydrophthalazinediones, e.g., luminol For a review of various labeling or signal producing systems which may be used, see, U.S. Pat. No. 4,391,904, incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label.

In some embodiments, the method also includes the step of imaging the cancer tissue in the subject using an imaging device an effective amount of a filamentous plant virus carrier is administered subsequent to administering an effective amount of the filamentous plant virus carrier to the subject. Examples of imaging methods include computed tomography, positive emission tomography, and magnetic resonance imaging.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

Cytotoxic Compounds

In certain embodiments of the invention, the filamentous plant virus particles can be coupled or conjugated to one or more cytotoxic compounds. Cytotoxic compounds are compounds that inhibit cell growth or promote cell death when proximate to or absorbed by a cell. Suitable cytotoxic compounds in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic compound can be, by way of non-limiting example, an antitumor agent, a photoactivated toxin or a radioactive agent.

Preferred radionuclides for use as cytotoxic compounds are radionuclides which are suitable for pharmacological administration. Such radionuclides include $^{123}$I, $^{125}$I, $^{131}$I, $^{90}$Y, $^{211}$At, $^{67}$Cu, $^{186}$Re, 188Re, $^{212}$Ph, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At can be conjugated to filamentous viral particles for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodo-3-pyridinecarboxylate (SIPC). Any iodine isotope can be utilized in the recited iodo-reagents. Other radionuclides can be conjugated to the filamentous plant virus particles by suitable chelation agents known to those of skill in the nuclear medicine arts.

Cytotoxic compounds include small-molecule drugs such as methotrexate, and pyrimidine and purine analogs, referred to herein as antitumor agents. Preferred chemotoxin differentiation inducers include phorbol esters and butyric acid. Antitumor agents can be directly conjugated to the filamentous plant virus particles via a chemical linker, or can encapsulated in a carrier, which is in turn coupled to the filamentous plant virus particle.

Preferred toxin proteins for use as cytotoxic compounds include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the patient, especially if injected intravascularly, it is preferred that they be encapsulated in a carrier for coupling to the filamentous plant virus particles.

Filamentous plant virus carriers including cytotoxic compounds can be used to treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the filamentous plant virus carriers including cytotoxic compounds are used to treat or image cancer tissue selected from the group consisting of colon cancer, brain cancer, breast cancer, fibrosarcoma, and squamous carcinoma.

Immune Response to Virus Particles

In some embodiments, administering the filamentous plant virus carrier to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the filamentous plant virus carrier is typically undesirable. Accordingly, in some embodiments it may be preferable to modify the filamentous plant virus carrier or take other steps to decrease the immune response. For example, an immunosuppressant compound can be administered to decrease the immune response. More preferably, the filamentous plant virus carrier can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the filamentous plant virus carrier is decreased by PEGylation. PEGylation is the process of covalent attachment of polyethylene glycol (PEG) polymer chains to a molecule such as a filamentous plant virus carrier. PEGylation can be achieved by incubation of a reactive derivative of PEG with the filamentous plant virus carrier. The covalent attachment of PEG to the filamentous plant virus carrier can "mask" the agent from the host's immune system, and reduce production of antibodies against the carrier. PEGylation also may provide other benefits. PEGylation can be used to vary the circulation time of the filamentous plant virus carrier. For example, use of PEG 5,000 can provide a virus carrier with a circulation half-life of about 12.5 minutes, while use of PEG 20,000 can provide a virus carrier with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the filamentous plant virus carrier. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Administration and Formulation of Filamentous Plant Virus Carriers

In some embodiments, the filamentous plant virus carrier is administered together with a pharmaceutically acceptable carrier to provide a pharmaceutical formulation. Pharmaceutically acceptable carriers enable the filamentous plant virus carrier to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the filamentous plant virus carrier into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated virus carrier can be administered as a single dose or in multiple doses.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the filamentous plant virus carrier vary depending upon many different factors, including means of administration, target site, physiological state of the patient, whether the patient is human or an animal, other medications administered, and whether treatment is prophylactic or therapeutic.

For administration for targeting or imaging in a mammalian subject or an avian subject utilizing a filamentous plant virus carrier, the dosage of the imaging or cytotoxic agent ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of virus particle is used to provide the desired dosage. An exemplary treatment regime entails administration once per every two weeks or once a month or once every 3 to 6 months. The filamentous plant virus carrier is usually administered on multiple occasions. Alternatively, the filamentous plant virus carrier can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following examples. It is to be understood that the particular examples, materials, amounts, and procedures are to be interpreted broadly in accordance with the scope and spirit of the invention as set forth herein.

EXAMPLES

Example 1

Increased Tumor Homing and Tissue Penetration of the Filamentous Plant Viral Nanoparticle Potato Virus X CPMV and PVX propagation. CPMV was propagated in cowpea plants (*Vigna unguiculata*). Plants were infected with 100 ng/µl CPMV in 0.1 M potassium phosphate buffer (pH 7.0) by mechanical inoculation using a light dusting of carborundum; leaves were harvested 10-14 days post infection and purified using established procedures. Steinmetz et al., Nanomedicine 6, 351-64 (2011). Virus concentration in plant extracts was determined by UV/visible spectroscopy ($\varepsilon_{CPMV}$=8.1 mLmg$^{-1}$cm$^{-1}$). PVX was propagated in *Nicotiana benthamiana*, leaves were harvested 10-14 days post infection. Purification was as follows: 100 g of leaves were homogenized in a standard blender using 2 volumes of cold 0.5 M borate buffer (pH 7.8) and filtered through 2-3 layers of cheesecloth and pH was adjusted to 6.5 using 1 M HCl. 0.2% (w/v) ascorbic acid and 0.2% (w/v) sodium sulfite were added. Plant material was centrifuged at 5,500 g for 20 min and supernatant was collected. After adding NaCl 0.2 M and 8% (w/v) PEG (MW 8,000), the solution was centrifuged at 15,000 g for 15 min and the pellet was resuspended in 0.1% β-mercaptoethanol and 0.5 M urea followed by centrifugation at 8,000 g for 30 min. The supernatant was ultracentrifuged at 160,000 g for 3 hrs and the pellet was resuspended in 5 mL buffer overnight at 4° C., and then ultracentrifuged over a 10-40% sucrose gradient at 100,000 g for 2 hrs. Light scattering band was collected and dialyzed against 0.5 M borate buffer (pH 7.8). Virus concentration in plant extracts was determined by UV/visible spectroscopy ($\varepsilon_{PVX}$=2.97 mLmg$^{-1}$cm$^{-1}$).

Bioconjugate chemistry to modify CPMV and PVX with A647 and PEG. CPMV and PVX (at 2 mgmL$^{-1}$ in 0.1 M potassium phosphate buffer pH 7.0) were reacted with NHS-PEG5000 (NanoCS) and NHS-A647 (Invitrogen) using a one-pot synthesis protocol (FIG. 1A). Reagents were added in a 10% (v/v) final concentration of DMSO and incubated overnight at room temperature, with agitation. PEG and A647 (or A555) were added using a molar excess of 3,000 and 2,000, respectively, per CPMV. For PVX, a molar excess of 4,000 and 2,500 of PEG and A647 (or A555), respectively was added. CPMV has a molar mass of 5.6×10$^6$ gmol$^{-1}$, and PVX has a molar mass of 35×10$^6$ gmol$^{-1}$. VNP formulations were purified through dialysis and 10 kDa-cut off centrifugal filter units (Millipore). A647-CPMV-PEG5000 nanoparticles and A647-PVX-PEG5000 nanofilaments were characterized using a combination of UV/visible spectroscopy, fluorescence measurements, denaturing gel electrophoresis, zeta potential measurements, and transmission electron microscopy (TEM).

UV/visible spectroscopy. The number of A647 or A555 molecules per virion was determined by UV-vis spectroscopy measurement done using the NanoDrop. The particle concentrations were determined using VNP-specific extinction coefficients of 8.1 mLmg$^{-1}$cm$^{-1}$ (CPMV) and 2.97 mLmg$^{-1}$cm$^{-1}$ (PVX) at 260 nm Denaturing gel electrophoresis. SDS gel electrophoresis was carried out to analyze conjugation of PEG chains to individual coat proteins. 10 µg protein samples were analyzed on 4-12% NuPage gels (Life Technologies) in 1× MOPS SDS running buffer. Protein bands were visualized under white light after staining the gels with Coomassie blue (0.25% w/v).

Zeta potential measurements. Zeta potential measurements were carried out using a 90 Plus zeta potential analyzer (Brookhaven Instruments Co., USA) for A647-CPMV-PEG5000 nanoparticles and A647-PVX-PEG5000 nanofilaments (1.5 mL of a 0.1 mg mL$^{-1}$ and 0.05 mg mL$^{-1}$ solutions, respectively) with five measurements, each comprising 10 runs.

TEM. Diluted samples of A647-CPMV-PEG5000 nanoparticles and A647-PVX-PEG5000 nanofilaments (20 µL., 0.1 mg mL$^{-1}$) were negatively stained with of 2% (w/v) uranyl acetate for 2 min on a copper grid. Samples were analyzed using a Zeiss Libra 200FE transmission electron microscope operated at 200 kV.

Avian embryo tumor xenograft model. Fertilized chicken eggs (McKinley Hatchery, St. Mary's Ontario) were incubated in a rotary incubator (Berry Hill) under 70% humidity at 37° C. for four days and then were removed from their shell and placed in sterile covered dishes. Avian embryos were incubated 5 more days in stationary incubators (Berry Hill) with 70% humidity at 37° C. On day 9, approximately 1×10$^5$ HT1080GFP or HEp3GFP cells (which were cultured in DMEM medium with high glucose and L-glutamine, and supplemented with 10% FBS, 1% penicillin-streptomycin all from Life Technologies) were injected in between the CAM layers and incubated for a further 6 days in stationary incubators with 70% humidity at 37° C. to allow for tumor growth and vascularization. Embryos were then injected with a 100 µl mixture containing 120 µg of A555-PVX-PEG (490 A555/PVX) and 20 µg of A647-CPMV-PEG (60 A647/CPMV) in PBS (pH 7.4) to ensure delivery of equal number of particles. The embryos were imaged in each channel of interest before injection, right after injection, and each hour thereafter. Time-lapse images were captured with an epifluorescence wide-field microscope (Quorum; Zeiss Axio Examiner, Zeiss) and Volocity software v6.0.1 (Perkin Elmer) and further analyzed with Volocity. After 4 hours, the tumors were excised from the CAM, washed with PBS, and put into 10% sucrose and 3.7% formalin in PBS overnight at 4° C. to fix the tissues and preserve fluorescence. Tumors were then washed in PBS and embedded with OCT on dry ice. Eight micron frozen sections of the tumor were collected (Leica CM1850 cryostat), mounted in Prolong gold with DAPI (Life Technologies), and imaged using an epifluorescence wide-field microscope attached to a spinning disc confocal unit (Quorum; Yokogawa CSU 10, Yokogawa) with Volocity software. Quantitation of nanoparticle uptake in HT1080GFP and HEp3GFP tumor xenograft models was determined by additional analysis of the acquired images in Volocity. Mean fluorescence within the tumor and core were quantified and further analyzed in GraphPad Prism v5.

Pharmacokinetics. Pharmacokinetics were evaluated using 8-week old healthy Balb/c animals (Charles River, Mass.). Following administration of A647-CPMV-PEG5000 and A647-PVX-PEG5000 formulations (200 µg/100 µL) via tail vein injections, blood was collected over a period of 60 minutes through retro-orbital bleeding in mice using heparin-coated tubes (Fisher); 2 time points were taken per mouse. Plasma was recovered from the blood via centrifugation at 16000 g for 10 mins. Fluorescence intensity (Ex/Em wavelengths 600/665) was measured using a Tecan microplate plate reader.

Tumor homing of CPMV versus PVX using the NCR nu/nu mice with HT-29 xenografts. HT-29 cells (ATCC) were cultured in RPMI medium supplemented with 10% FBS, 1% penicillin-streptomycin, and 1% L-glutamine at 37° C. in 5% $CO_2$ (tissue culture reagents were supplied from Life Technologies). Tumors were induced through subcutaneous injection of $5\times10^6$ cells/50 µL RPMI mixed with an equal volume of matrigel (Fisher). Six-week old NCR nu/nu mice were xenografted with HT-29 tumors on each flank. To reduce tissue auto fluorescence, animals were maintained on an alfalfa free diet (Teklad) for two weeks prior to VNP administration. Animals were monitored and tumor size measured using calipers. Tumors were allowed to reach an average volume of 20 $mm^3$ (10-12 days). A647-CPMV-PEG5000 (52 A647/CPMV) and A647-PVX-PEG5000 (385 A647/PVX) were administered intravenously at 200 µg in 100 µL of sterile PBS per mouse (n=3 animals per group; groups: PBS, CPMV, and PVX). To ensure maximum tissue accumulation, animals were analyzed at t=24 hrs post administration. Two methods were used to analyze tissue distribution based on fluorescence: (1) animals were sacrificed and brain, heart, lungs, spleen, kidneys, liver, as well as the tumors on the flanks were excised and imaged using Maestro™ fluorescence imaging instrument (using yellow excitation and emission filters with a 800 ms exposure time), and (2) tissues were collected, the weight recorded, and tissues were homogenized in PBS. Homogenates were centrifuged for 10 min at 13,000 g to remove non-homogenized tissue. Fluorescence intensity (Ex/Em wavelengths 600/665) was measured using a Tecan microplate plate reader. Data were normalized against tissue weight.

Immunohistochemistry. Intra-tumoral localization of CPMV and PVX was carried out using immunohistochemistry. Ten-micron thick tumor sections were prepared on a Leica CM1850 cryostat and fixed with 95% ethanol for 20 min in ice. Sections were then permeabilized with 0.2% Triton X-100 (EMD Chemicals) in PBS for 2 mins and rinsed with PBS. Blocking was done with 10% goat serum (GS) (Life Technologies) in PBS. Endothelium was immunostained using a FITC-labeled CD31 antibody (Biolegend) (1:250) with 1% GS for lh at room temperature (RT). The sectioned were rinsed thrice with PBS and nuclei were stained with DAPI (MP Biomedicals) (1:9500 in PBS) for 10 min at RT, followed with another round of rinsing with PBS. The sections were covered with Permount mounting media (Fisher). The slides were stored at −20° C. until imaged. Confocal analysis of the stained tissue sections was carried out on Olympus FV1000 laser scanning confocal microscope.

Results and Discussion

Production of CPMV and PVX. CPMV particles and PVX filaments were purified from infected *Vigna unguiculata* and *Nicotiana benthamiana* plants, respectively, yielding 0.5-1 mg VNPs per 1 g infected leaves. Virus concentration in plant extracts was determined by UV/visible spectroscopy (CPMV $\varepsilon_{260\,nm}$=8.1 $mLmg^{-1}cm^{-1}$ and PVX $\varepsilon_{260\,nm}$=2.97 $mLmg^{-1}cm^{-1}$). The purity of the VNP preparation was confirmed based on the A260:A280 ratio (a ratio of 1.8 indicates pure and intact CPMV particles, and a ratio of 1.2 indicates pure and intact PVX filaments). Structural integrity of the purified VNPs was further confirmed using transmission electron microscopy (TEM) as well as size-exclusion chromatography (SEC).

Chemical modification of CPMV and PVX with polyethylene glycol (PEG) and Alexa Fluor 647 (A647). VNPs are particulate and proteinaceous structures with high degree of symmetry and polyvalency. VNPs are thus intrinsically immunogenic materials. The immunogenicity of VNPs and many other proteinacous therapies can be significantly reduced through PEGylation. Le et al., J Control Release 108, 161-177 (2005). The PEGylation of VNPs also reduces undesirable non-specific cell interactions, prolongs plasma circulation and increases stability. Steinmetz, N. F. & Manchester, M., Biomacromolecules 10, 784-792 (2009). PEG is thus an important component when developing VNPs as contrast agents or drug delivery vehicles. Alexa Fluor 647 (A647) was also used; this near-infrared dye is commonly used for molecular imaging applications and shows compatibility with the VNP carrier system as well as with fluorescent imaging modalities used in preclinical imaging, i.e. intravital microscopy and Maestro™ imaging system.

In this study, CPMV and PVX were labeled with PEG5000 and A647 (and A555) at solvent-exposed surface Lys residues using NHS active probes (FIG. 1A). Purified A647-CPMV-PEG and A647-PVX-PEG were characterized using a combination of UV/visible spectroscopy, TEM, denaturing gel electrophoresis, and zeta potential measurements (FIG. 1). TEM confirmed that VNPs remained structurally sound after chemical modification (FIG. 1B). UV/visible measurements and electrophoresis of protein subunits confirmed that both labels, A647 and A555, and PEG5000, were covalently attached. The number of dye moieties per VNP was calculated based on the UV/visible spectrum using the concentration ratio of dye to VNP. The concentrations were calculated using Beer-Lambert law and the respective extinction coefficients: A647 $\varepsilon_{650\,nm}$=270,000 $M^{-1}cm^{-1}$, CPMV $\varepsilon_{260\,nm}$8.1 $mLmg^{-1}cm^{-1}$, and PVX $\varepsilon_{260\,nm}$=2.97 $mLmg^{-1}cm^{-1}$. Denaturing gel electrophoresis confirmed covalent modification of the coat proteins with A647 (this is based on the bright blue coloration of the protein bands when visualized under white light). Lower mobility bands indicate successful PEGylation (FIG. 1C). Protein band intensity profile analysis using ImageJ software and Coomassie-stained gels was used to determine the degree of PEGylation.

The inventors found that CPMV was labeled with 53 A647 dyes and 35 PEG5000 chains. PVX was found to display 386 A647 dyes and 380 PEG5000 chains. The reproducibility of generating these formulations lies within a 10% error range with regard to the number of fluorophores and PEG chains attached. CPMV consists of 60 copies each of a small and a large protein arranged in a pseudo T=3 symmetry; and PVX is formed by 1270 identical copies of a single coat protein arranged in helical structure. Data indicate similar degree of PEGylation comparing CPMV and PVX; in each case approximately 30% of the coat proteins were labeled with PEG5000 chains (see also band intensity profile, FIG. 1C). Considering the differences in molar mass of CPMV and PVX; the dye per protein ratio is comparable; 7.3× the number of dyes were attached to the 6.3× higher molecular weight macromolecule formed by PVX compared to CPMV (CPMV has a molar mass of $5.6\times10^6$ $gmol^{-1}$, PVX has a molar mass of $35\times10^6$ $gmol^{-1}$).

Overall engineered CPMV and PVX displayed similar degrees of surface modification with dyes and PEG. Of course, one has to take under consideration that each VNP is built from different coat protein building blocks and that ligand presentation differs based on the different geometrical shapes of the VNPs. Surface charge, in addition to carrier geometry, is an important factor to consider when comparing different materials. Therefore the zeta potential of A647-CPMV-PEG and A647-PVX-PEG (FIG. 1D) was determined Fluorescent and PEGylated CPMV has a negative zeta potential of −16.4±2.6 mV, whereas PVX has a positive zeta potential of 24.9±8.2 mV. This is interesting considering that the reported isoelectric point of both VNPs are similar: the isoelectric point of CPMV lies between pH 3.4-4.5 and the isoelectric point of PVX is reported at pH 4.4. When comparing these two VNPs differences in shape and zeta potential have to be taken into account (see discussion below).

It is important to note, that in previous studies using PVX conjugated with A647 and PEG, an unexpected phenomenon was observed. When PVX was conjugated to A647 and PEG1000 cell interactions were reduced, as expected. However, when PVX was conjugated with A647 and PEG2000, increased cell interactions were reported. Steinmetz, N. F. & Manchester, M., Biomacromolecules 10, 784-792 (2009). This was demonstrated using HeLa and BalbC17 cells. It was hypothesized that the PEG2000 layer somehow stabilizes the A647 dye presentation on the VNP leading to enhanced interactions of the hydrophobic flat molecule with the cell membrane. In the studies described herein, the PVX design was revised and incorporated PEG5000 (rather than PEG2000). It was hypothesized that the larger PEG chains would efficiently cover the PVX rod including the A647 dyes and thus efficiently shield the nanomaterial from cellular interactions. Indeed, this was confirmed using several mammalian cell lines that PVX-A647-PEG5000 is effectively shielded. The previously described phenomena are attributed to the specific combination of PVX and A647 and PEG2000. Since shielding on reduced cell interactions of A647-PVX-PEG5000 were confirmed, it is unlikely the in vivo properties of A647-PVX-PEG5000 are directed by the A647 fluorophore. The observations described below can be attributed to the physical and chemical differences CPMV and PVX carriers.

Figure 2:
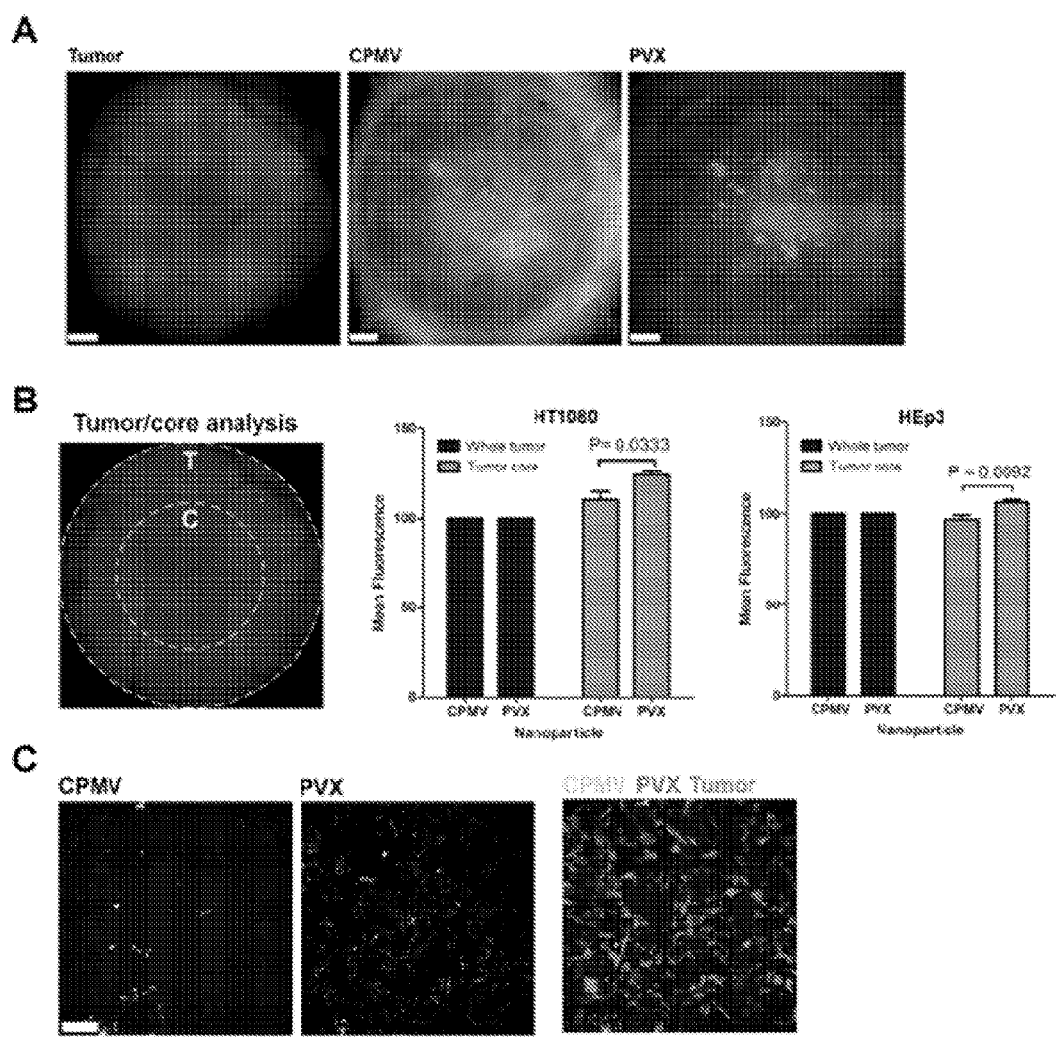
FIG. 2 provides an image and graphs showing intravital imaging of VNP uptake in human tumor xenografts in the CAM. A) Avian embryos bearing vascularized GFP-expressing human fibrosarcoma HT1080 or human epithelial carcinoma HEp3 tumors (left) were co-injected with 120 μg of PVX-PEG-A555 (right) and 20 μg of CPMV-PEG-647 (middle) and visualized 4 hr after injection. Scale bar=190 μm. B) The analysis of whole tumor uptake of CPMV and PVX nanoparticles compared to uptake only in the tumor core was assessed using distinct ROIs (left panel) in HT1080 (middle panel) and HEp3 (right panel) tumors. While whole tumor localization of CPMV and PVX were comparable, PVX accumulated in the core of tumors to a significantly higher degree than CPMV (unpaired t test). C. The localization of nanoparticles was assessed in 8 micron sections of the tumor core using fluorescence microscopy. CPMV and PVX are visualized in the tumor. While CPMV was visualized in punctate foci, PVX was distributed throughout the tumor in areas devoid of CPMV.

Tumor homing and penetration of PVX versus CPMV in the avian embryo tumor xenograft model. Tumor homing and tissue penetration properties of CPMV and PVX VNPs were evaluated using human fibrosarcoma (HT1080) and squamous carcinoma (HEp3) tumor models. To evaluate tumor uptake in real time, intravital microscopy was carried out over a 4-hour time frame. The two VNPs were labeled with spectrally distinct fluorophores; A647-CPMV-PEG and A555-PVX-PEG were synthesized. This allowed for a direct side-by-side comparison of the two VNP platforms after co-injection. The amount of VNP administered was adjusted to give equal number of moles of VNP/animal, i.e. 120 µg of PVX and 20 µg CPMV were administered ($3.5 \times 10^{-12}$ moles VNP/animal). Intravital imaging indicated that both PVX and CPMV accumulated in solid tumors after intravenous administration, however, the intra-tumoral localization was found to differ with PVX accumulating in the center of the tumor (FIG. 2). A comparable tumor distribution was observed for both fibrosarcoma and squamous carcinoma tumor models.

Systemic delivery of nanocarriers and their cargos to solid tumors is largely governed through the enhanced permeability and retention (EPR) effect. Iyer et al., Drug Discov Today 11, 812-818 (2006). EPR is characterized by increased vascular permeability and inefficient lymphatic drainage as a result of tumor hypervascularization. Nanomaterials passively target the tumor by extravasating from the tumor vasculature and accumulating in the tumor parenchyma. It has been shown previously that EPR-mediated accumulation of elongated nanomaterials is enhanced compared to spherical nanomaterials. Chauhan et al., Angew Chem Int Ed Engl 50, 11417-11420 (2011). In the CAM model, however, enhanced tumor accumulation of the PVX versus CPMV was not observed. On the other hand, PVX filaments were observed to home in on the tumor core, whereas CPMV nanoparticles were localized throughout the tissue with no apparent increase in the tumor center (FIG. 2). To further evaluate the intra-tumoral localization of PVX versus CPMV, tumors were collected, sectioned, and imaged using confocal microscopy. Consistent with findings from intravital imaging, PVX spread consistently throughout the tumor tissue and penetrated into areas in which CPMV was not apparent.

A growing body of data indicates that filamentous structures have better diffusion rates in fibrous matrices (e.g. collagen-rich tumor matrices) compared to globular materials, (Stylianopoulos, Biophys J 99, 3119-3128 (2010)) this may explain the observation that PVX penetrates deeper into the tumor tissue and accumulates in the tumor core. Besides the shape-derived advantages of PVX, surface charge-derived differences should also be considered. Consistent with these findings, others have reported enhanced tumor accumulation and penetration of positively-charged materials. The collagen-rich matrix is a major determinant of interstitial transport. Jain, R. K. & Stylianopoulos, Nat Rev Clin Oncol 7, 653-664 (2010). Collagen carries positive charges and negatively-charged materials can aggregate in the collagen matrix through electrostatic interactions, thus limiting their diffusion rates. Cationic nanoparticles have enhanced tumor homing properties and also exhibit higher vascular permeability compared to their anionic counterparts. Stylianopoulos et al., Biophys J 99, 1342-1349 (2010).

The positive zeta potential of PVX thus could further provide an advantage in addition to its flexible, high aspect ratio shape. Future experiments are required to separate charge and shape; this could be achieved through the display of negatively charged surface groups on PVX to invert its zeta potential. Alternatively, icosahedrons of the same size but opposite zeta potential could be evaluated, e.g. CPMV and Brome mosaic virus (BMV).

Tumor homing of CPMV versus PVX using the NCR nu/nu mice with HT-29 xenografts. Next, tumor homing and biodistribution of VNPs were evaluated using an animal model of colon cancer, specifically NCR nu/nu mice with human HT-29 xenografts. Tumors were allowed to reach an average volume of 20 mm³ (10-12 days) prior to administration of the VNPs. Quantitative studies were conducted using a combination of Maestro™ Imaging system and plate reader assays. The amount of protein and dyes were kept constant, i.e. 200 µg of A647-CPMV-PEG and A647-PVX-PEG, respectively were administered intravenously. Co-injection could not be performed. Even when animals were kept on an alfalfa-free diet the background fluorescence from tissues was too high for using dyes such as A488 or A555. Therefore both VNPs were labeled with A647 and evaluated side-by-side.

Figure 3:
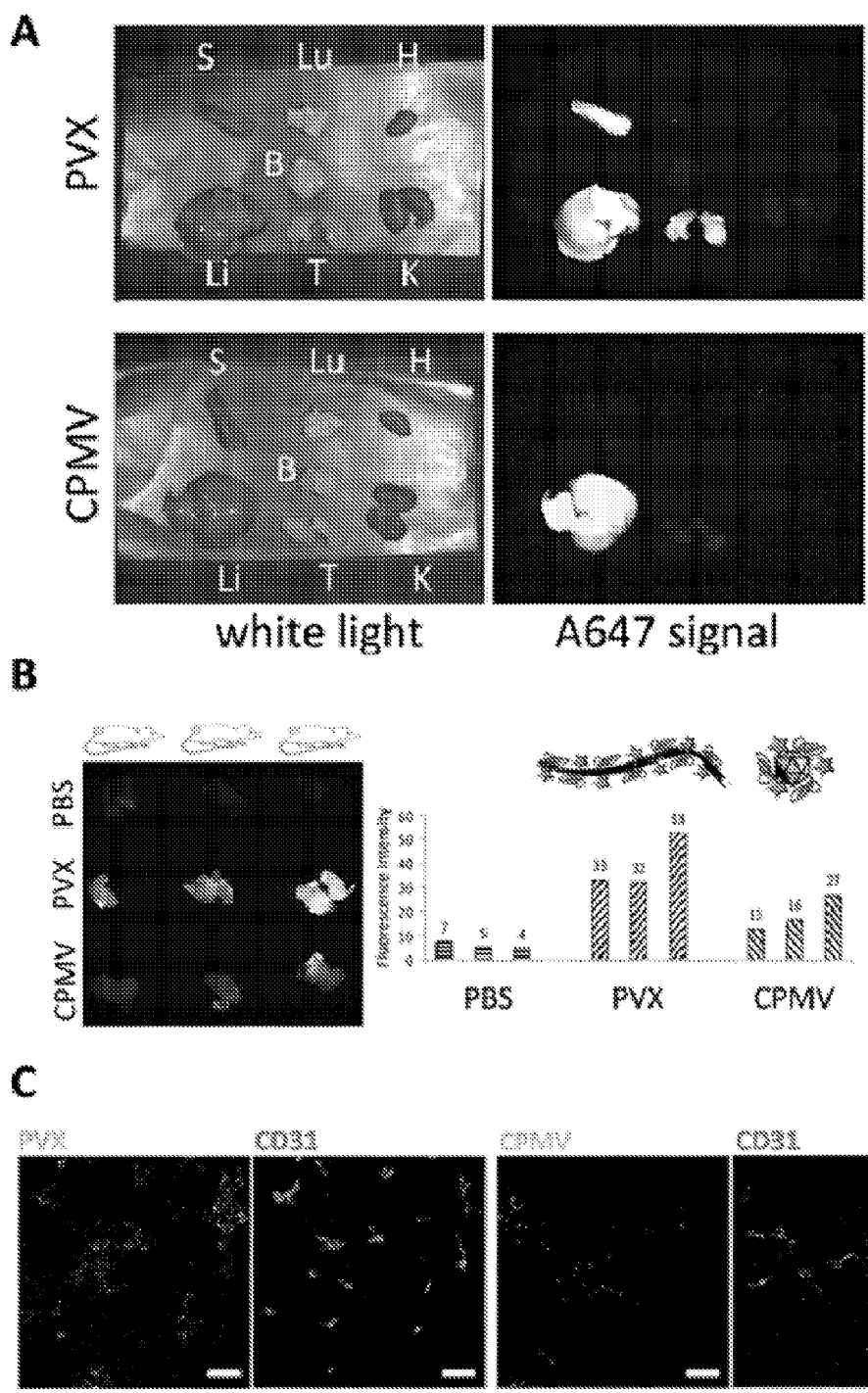
FIG. 3 provides images and graphs showing tumor homing and biodistribution of VNPs measured using Maestro™ Imager, with A) showing A647-labeled and PEGylated CPMV and PVX were administered intravenously into nude mice bearing HT-29 xenografts. 24-hours post-injection tissues were collected and imaged; tissues are shown under white light and fluorescence (A647 signal); B) showing tumors (2 per animal) were exercised from 3 animals and imaged; qualitative data (left) and quantitative data (right) are presented; and C) showing intra-tumoral localization of CPMV and PVX. Endothelium was immunostained using a FITC-labeled CD31 antibody. Nuclei were stained with DAPI. Scale bars are 30 microns.
Figure 4:
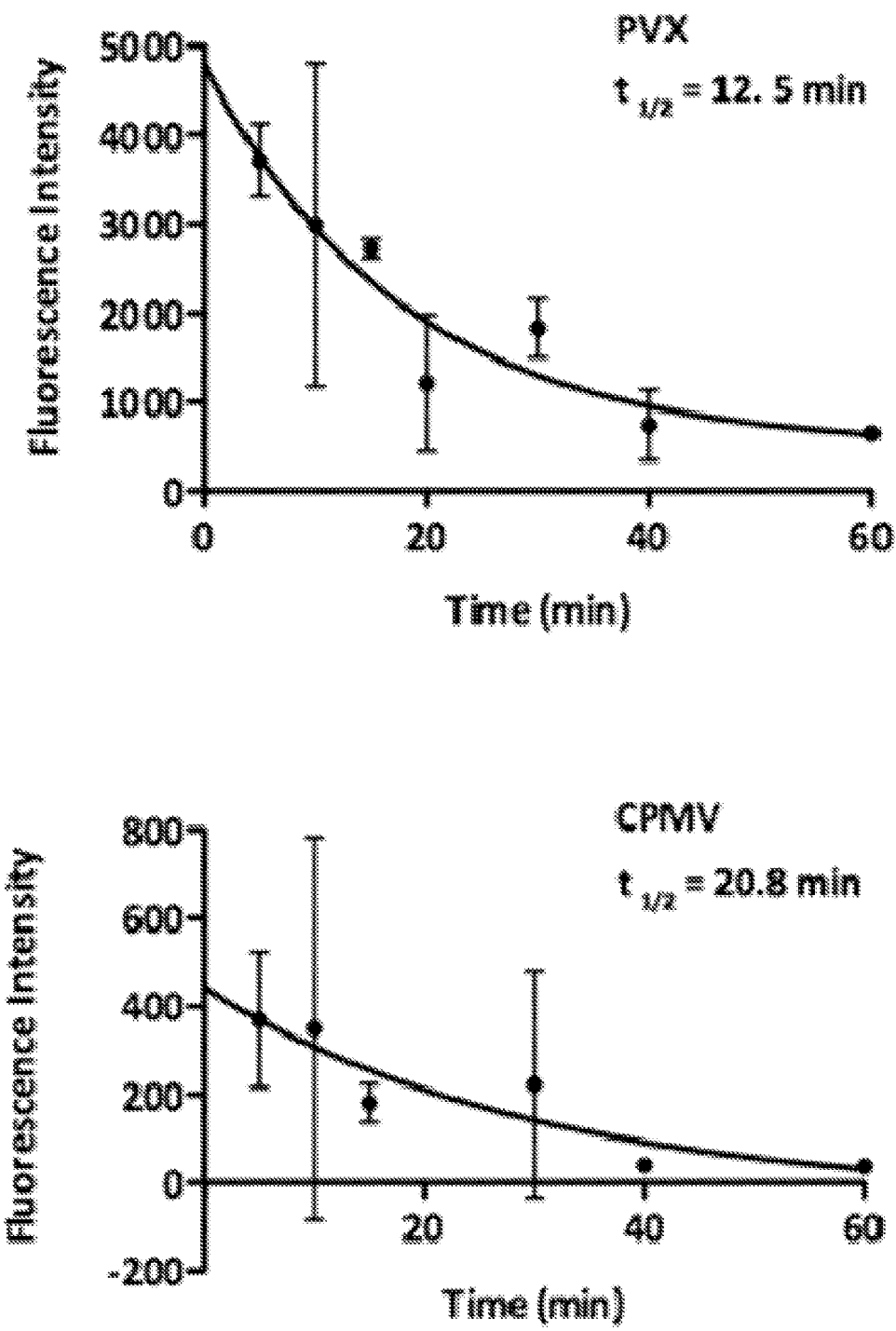
FIG. 4 provides graphs showing the plasma clearance of A647-labeled, PEGylated PVX and CPMV. Pharmacokinetics were evaluated using healthy Balb/c mice. Blood was collected over a 60-min time period, plasma extracted and the fluorescence intensity measured.
Figure 5:
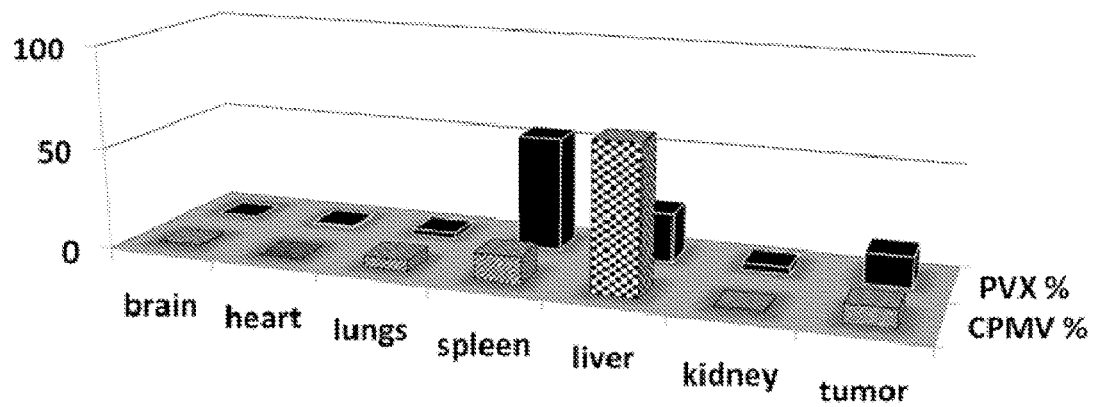
FIG. 5 provides graphs showing the biodistribution of A647-labeled and PEGylated CPMV and PVX nanoparticles and filaments. Three nude mice with human HT-29 tumor xenografts each were injected with PBS (control group), CPMV, and PVX. Tissues were collected and analyzed 24 hours post administration. Fluorescence intensity normalized per gram of tissue weight is plotted for all major organs and tumors for each mouse; and the average biodistribution normalized against PBS samples. The percentage of VNPs detected in each tissue is shown for each organ and tumors analyzed.

It was found that, using the HT-29 tumor mouse model, PVX showed enhanced tumor homing compared to CPMV. Furthermore, the two VNPs show distinct biodistribution profiles (FIGS. 3-5). Results from imaging (FIG. 3) and quantitative biodistribution (FIG. 5) are in good agreement and it appears that CPMV nanoparticles are mostly localized to the liver with negligible tumor accumulation. In stark contrast, PVX showed enhanced tumor homing; PVX nanofilaments were also taken up by liver and spleen. The co-localization of A647-PVX-PEG with biomarkers is also shown in Table 1, below:

TABLE 1

Co-localization of A647-PVX-PEG with biomarkers in liver, spleen and tumors.

| Organ | Biomarker | Mander's coefficients 24 h | 72 h |
|---|---|---|---|
| Liver | F4/80 | 0.351 | 0.913 |
| | CD31 | 0.976 | 0.379 |
| Spleen | F4/80 | 0.152 | 0.023 |
| | CD31 | 0.053 | 0.044 |
| | B220 | 0.866 | 0.762 |
| | CD223 | 0.007 | 0.059 |
| | CD3 | 0.006 | 0.021 |
| | CD21/35 | 0.964 | 0.098 |
| HT29 Tumors | CD31 | 0.54 | 0.068 |
| | B220 | 0.465 | — |
| | F4/80 | 0.345 | — |
| 4T1 Tumors | CD31 | 0.367 | — |
| | B220 | 0.574 | — |
| | F4/80 | 0.324 | — |
| Gli36Δ5 Tumors | CD31 | 0.855 | — |
| | B220 | 0.108 | — |
| | F4/80 | 0.264 | — |

Studying the intra-tumoral localization of A647-CPMV-PEG and A647-PVX-PEG on sectioned tumor tissues, it was found that neither formulation was confined within the endothelium. PVX accumulation is more profound and it appears that PVX shows enhanced tissue penetration compared to CPMV; these findings are consistent with data from the avian tumor model (see FIG. 2).

The enhanced tumor homing of PVX to solid tumors is consistent with reports on synthetic nanomaterials. Successful tumor delivery requires nanoparticles to enter tumor microcirculation followed by extravasation into tumor tissue. The fate of the nanoparticle depends on its ability to drift laterally toward the tumor blood vessel in order to extravas ate into the surrounding tumor tissue. Filamentous rods have favorable margination properties compared to their spherical counterparts. Lee et al., Nanotechnology 20, 495101 (2009). It also has been suggested that nanofilaments penetrate tumor better compared to spherical nanomaterials thus further enhancing tumor retention, due to differences of nanoparticle versus nanofilament transport across membranes.

Enhanced plasma circulation times also can enhance tumor homing via EPR effects. Nanofilaments and rod-shaped materials tend to evade phagocytosis and thus have enhanced circulation times. Interestingly, the data indicates that PEGylated and fluorescently-labeled CPMV, with a plasma half life of $t_{1/2}$=20.8 min, has a slightly longer plasma circulation time than PVX, which has a $t_{1/2}$=12.5 min (FIG. 4). High accumulation of PVX was also observed in the spleen (FIGS. 3 and 5). Previous studies have indicated that positively-charged materials show prolonged plasma circulation times. Netti et al., Cancer Res 60, 2497-2503 (2000). Therefore, it is somewhat surprising that filamentous PVX, with its high aspect ratio and high positive charge density does not show enhanced pharmacokinetics. Clearly, the inventors data indicate that the enhanced tumor accumulation of PVX is governed by an alternate mechanism than enhanced plasma circulation time, and that the high uptake of PVX in the spleen may indicate rapid clearance through macrophages.

Biodistribution of CPMV and PVX is distinct. To gain further insight into the in vivo behavior of these VNPs, biodistribution was evaluated using fluorescently-labeled and PEGylated VNPs. At 24 hours post-intravenous administration, tissues were collected, digested, and the fluorescence intensity normalized to organ weight determined (FIG. 5). CPMV accumulates predominantly in the liver (71% of administered CPMV is detected in the liver), while smaller amounts are detected in the spleen (13%) and 9% of the particles are localized to the tumor. PVX also accumulated in the liver (55%), however a significant amount is also found in the spleen (23%) and tumor homing is also enhanced with 15% of the administered dose (FIG. 5).

Biodistribution of CPMV has been reported previously. CPMV has broad biodistribution and using PCR-based methods it could be detected in a wide variety of tissues throughout the body with no apparent toxic effects. Kaiser et al., Int J Nanomedicine 2, 715-733 (2007). Quantitative data indicated that CPMV particles mostly accumulated in the liver with some accumulation in the spleen. This is in good agreement with the findings (FIG. 3+5). PVX also accumulates in the liver but also shows significant localization in the spleen. Uptake and accumulation of VNPs in organs with filtration function such as liver and spleen is expected. These organs are part of the reticuloendothelial system (RES), which is a component of the immune system. Its function is to remove antigens, such as proteinaceous nanoparticle structures, from circulation. The fact that enhanced tumor homing was not observed in the CAM model could be explained by the differences in uptake by the RES, which is less developed in this embryonic model. Differences in the tumor homing profiles of CPMV and PVX were also observed in the CAM model. The high uptake of PVX in the spleen and its short plasma circulation time may indicate rapid clearance through macrophage uptake.

Conclusion

The filamentous, high aspect ratio PVX VNP platform shows enhanced tumor homing and tissue penetration properties compared to CPMV, the prototypical plant VNP. The data suggest that there are shape- and surface charge-derived advantages of PVX for in vivo applications. The high accumulation of PVX in the spleen suggests rapid clearance through macrophage uptake and could be related to the immunogenicity of the platform. Because PEGylation of the VNPs is expected to reduce macrophage uptake and interaction with cells of the immune system, it will be useful to evaluate the histopathology and immunogenicity of PVX in detail. Indeed, as the design principles are explored to engineer PVX as a drug delivery system, it will be important to achieve the correct balance between systemic clearance, tumor homing and tissue penetration. Filamentous VNP formulations have advantages beyond their physical and tumor homing properties. Rods have a much larger surface area than spherical particles, thus offering more potential acceptor sites for functionalization, and therefore greater loading with targeting ligands, imaging reagents and/or drugs. Rod-shaped particles also present ligands in a more efficient manner. Cells are typically 10-100 times larger than a nanostructure, and the cell surface tends to be relatively flat. A rod-shaped structure may in theory interact with a larger number of binding sites on the cell surface, thus potentially increasing targeting sensitivity and specificity. PVX is a promising new plant VNP technology, and the work presented here is in good agreement with the emerging paradigm that rod-shaped nanomaterials are advantageous for nanomedical applications.

Example 2

Biodistribution and Clearance of a Filamentous Plant Virus in Healthy and Tumor-bearing Mice The enhanced tumor homing properties of PVX combined with its large surface area offering a higher loading capacity for cargos renders PVX is an attractive platform for the development of novel nanomedical formulations. Herein, PVX biodistribution and clearance in healthy mice and mouse models of colon, breast, and brain cancer is described. A combination of ex vivo whole-organ imaging, quantitative fluorescence assays on homogenized tissues and immunofluorescence microscopy provides detailed analysis of the in vivo fate of PVX over a 5-day time course. The data gained provide fundamental information of the in vivo behavior of PVX, essential for further tailoring and development of the platform for potential clinical applications.

Methods

PVX propagation. PVX was propagated in *Nicotiana benthamiana*. Leaves were harvested 10-14 days after mechanical inoculation with 5 µg of purified PVX particles. PVX was purified as described earlier.

Bioconjugate chemistry to modify PVX with A647 and PEG. Purified PVX was prepared at a concentration of 2 mg mL$^{-1}$ in 0.1 M potassium phosphate buffer (pH 7.0) and was incubated with NHS-PEG5000 (NANOCS) and NHS-A647 (Life Technologies) using a one-pot synthesis protocol. The reagents were added to a 10% (v/v) final concentration in DMSO and incubated overnight at room temperature, with agitation. PEG and A647 were added at a molar excess of 4000 and 2500, respectively (PVX has a molar mass of $3.5 \times 10^7$ g mol$^{-1}$). VNP formulations were purified by dialysis and 10 kDa cut-off centrifugal filtration (Millipore).

UV/visible spectroscopy. Labeling efficiency with fluorophores was determined by UV/visible spectroscopy using a NanoDrop instrument. The number of A647 labels per virion was calculated based on the Beer-Lambert law using the specific extinction coefficients for PVX (2.97 mL mg$^{-1}$cm$^{-1}$ at 260 nm) and A647 (270,000 M$^{-1}$cm$^{-1}$ at 650 nm).

Denaturing gel electrophoresis. Denaturing sodium dodecylsulfate polyacrylamide gel electrophoresis (SDS-PAGE) was used to confirm the conjugation of PEG chains to individual coat proteins. The inventors analyzed 10 µg of denatured protein samples on 4-12% NuPage gels (Life Technologies) in 1x MOPS SDS running buffer (Life Technologies). Protein bands were visualized under white light after staining with Coomassie Brilliant Blue (0.25% w/v).

Transmission electron microscopy. Diluted samples of A647-PVX-PEG5000 nanoparticles (20 µL, 0.1 mg mL$^{-1}$) were negatively stained with 2% (w/v) uranyl acetate for 2 min on a carbon-coated copper grid. Samples were analyzed using a Zeiss Libra 200FE transmission electron microscope at 200 kV.

PVX biodistribution. All animal studies were carried out using IACUC approved procedures. The biodistribution of A647-PVX-PEG particles in BALB/c mice was profiled by ex vivo fluorescence imaging of intact tissues using the Maestro Imaging System, or quantitative fluorescence detection in tissue homogenates using a Tecan fluorescence plate reader.

Tumor homing and imaging using mouse xenograft models: Tumor homing was investigated using subcutaneous mouse human tumor xenografts models of colon (HT-29) and brain cancer (Gli36A5) in NCr nu/nu nude mice and orthotopic 4T1 mammary tumor xenografts in 8-week-old female BALB/c mice.

Immunofluorescence and confocal and fluorescence microscopy: The inventors prepared 10 µm cryosections from frozen isolated organs using a Leica cryomicrotome. After fixation, frozen tissue sections were stained for different markers including CD31 (endothelial cells), F4/80 (macrophages), CD3 (T-cells), CD45R/B220 (B-cells follicles), and LAG-3/CD223 (activated T-cells) using combinations of primary and secondary antibodies (see supporting information for details). Slides were analyzed using a Zeiss Axio Observer Z1 motorized FL inverted microscope and by confocal microscopy using a Fluoview FV1000 (Olympus).

Results and Discussion

Production of PVX. PVX filaments were isolated from infected *Nicotiana benthamiana* plants, yielding 0.5-1 mg pure PVX per gram of infected leaves. The concentration of PVX in plant extracts was determined by UV/visible spectroscopy using the PVX extinction coefficient of 2.97 mg$^{-1}$ mL cm$^{-1}$. The purity of the PVX preparation was confirmed based on the A260:A280 ratio of 1.2, indicating pure and intact PVX filaments. The structural integrity of the purified VNPs was also confirmed by TEM analysis.

Chemical modification of PVX with PEG5000 and A647. PVX has an aspect ratio of 40, reflecting its filamentous structure (515×13 nm). Each filament comprises 1270 identical copies of a single 25-kDa coat protein. Bioconjugation using N-hydroxysuccinimide (NHS) active esters targeting solvent-exposed lysine side chains allows the functionalization of each coat protein. PVX was conjugated with the near-infrared fluorophore A647 to allow the imaging and tracking of the formulations, and also with PEG to enhance particle solubility and stability. A647 and PEG5000 were chosen because the inventors had recently determined that A647-PVX-PEG is suitable for tumor homing and imaging in preclinical tumor animal models. See Example 1. The PVX formulation was therefore designed according to previous procedures. TEM imaging confirmed that the particles maintained their structural integrity and filamentous shape after modification. The appearance of higher-molecular-weight protein bands following denaturing SDS-PAGE indicated covalent attachment of PEG5000 chains to PVX as anticipated. The multiple bands suggested that PEGylation may prevent the complete denaturation of PVX capsids into single-copy coat proteins, i.e. the higher-molecular-weight bands are likely to be dimers of PEGylated coat proteins. The intensity of the bands was measured using ImageJ software to determine the degree of PEGylation, and found that ~30% of the coat proteins were modified with PEG, equivalent to ~380 PEG5000 chains per PVX particle. UV/visible spectroscopy was used to determine the number of dye labels per PVX particle using the corresponding extinction coefficients and the Beer-Lambert law. It was found that the density of A647 was similar to PEG5000, i.e. 380 A647 labels per PVX. The chemical conjugation was highly reproducible, with only 10% batch-to-batch variation. This density of A647 labeling yields intensely fluorescent PVX nanofilaments that do not undergo fluorescence quenching. The zeta potential of the particles suspended in PBS buffer (pH 7) was measured to be 24.9±8.2 mV.

To summarize, Equal densities of PEG5000 and A647 fluorophore were bioconjugated to PVX; i.e. ~380 molecules of each, which equates to 30% of the coat proteins modified with PEG and an additional 30% of the coat proteins modified with A647.

Biodistribution of PVX. Several methods are available to study the biodistribution of nanoparticles and their cargos, including high-performance liquid chromatography (HPLC), inductively-coupled plasma atomic emission spectroscopy/mass spectroscopy (ICP-AES/MS), radiolabeling followed by scintillation counting positron emission tomography (PET), and fluorescence-based assays. The latter approach has gained popularity because it is rapid and inexpensive. Nanomaterials can also be labeled with near-infrared dyes suitable for live imaging, ex vivo whole-organ imaging and the quantitative analysis of fluorescence in tissue homogenates. Artzi et al., Nat Mater 10(9), 704-709 (2011).

The biodistribution of A647-PVX-PEG was studied using a combination of quantitative plate-reader assays and ex vivo imaging of whole organs. For the quantitative assays, A647-PVX-PEG was administered at 10 mg/kg body weight into the tail veins of BALB/c mice, and the brain, lungs, heart, kidneys, liver and spleen were removed and homogenized at time intervals of 2, 6, 24 and 48 h (n=4 per time point). The fluorescence signals were normalized against tissues from animals injected with PBS and the fluorescence intensity per gram of tissue weight (FI/gram) was determined (FIG. 6A). For the whole-organ assays, A647-PVX-PEG was administered as described above and organs were removed for imaging using the Maestro system 24 h and 72 h after injection (n=3 per time point) (FIG. 6B).

As evident from the fluorescence data, there is some degree of variability between animals, especially at the early times points, i.e. 2 h versus 6 h post-administration. Overall the trend indicates PVX was cleared from the circulation and accumulated in spleen>liver>kidneys within 2-6 h post administration (FIG. 6A). Similarly high variations between animals were previously reported studying the CPMV nanoparticle platform described in Example 1. The earlier studies focused on the evaluation of only one PVX-based formulation modified with dyes and PEG; this formulation could be regarded as a universal platform for future cargo-loading and delivery. In all four animals studied, the trend was the same indicating sequestration of PVX within 2-6 h and in the mononuclear phagocyte system (MPS) of spleen and liver (FIG. 6A), consistent with the short half-life of A647-PVX-PEG of $t_{1/2}$=12.5 min.

At longer time points, i.e. 24-48 h signals fade indicating clearance from the body. The presence of fluorescence signals in the kidneys may also indicate renal clearance. Strong fluorescence signals in the stools of the animals also suggest processing and clearance through hepatobiliary system. Weak signals from the lungs were noted, consistent with previous reports on other elongated nanoparticles. Liu et al., Proc Natl Acad Sci USA 105(5), 1410-1415 (2008).

The plate reader assays showed that fluorescence signals could no longer be detected in tissues isolated 48 h post administration. Faded fluorescence signals could still be detected by Maestro ex vivo imaging at longer time points (72 h, FIG. 6B), indicating it may take several days for clearance of PVX from tissues (this is similar to observations made studying the in vivo fate of CPMV). A more sensitive assay may be required to determine the timing of clearance more accurately.

The in vivo fate of nanoparticles is governed by their physiological properties such as size, shape, composition, surface chemistry and physical properties. Li S D, Huang L., Mol Pharm 5(4), 496-504 (2008). The biodistribution profile observed for PVX matches previous reports for nanomaterials of similar size, shape and composition. Spherical nanomaterials 30-80 nm in diameter tend to be sequestered in the lungs and leaky vasculature, whereas those larger than 80 nm are generally trapped in the spleen and liver. Lunov et al., ACS Nano 5(3), 1657-1669 (2011). Nanomaterials similar in size to PVX are not usually excreted by the renal system but are mainly removed from circulation efficiently by the MPS. Sa et al., J Pharm Biomed Anal, 70, 602-4 (2012).

MPS versus renal clearance has been studied using carbon nanotubes, a synthetic class of high aspect ratio nanomaterials. Data remain elusive: while pristine SWCNTs showed significant accumulation in liver only, PEGylated SWCNTs were found in liver and spleen. Some functionalized SWCNTs and MWCNTs, on the other hand, showed efficient renal clearance. Modeling indicated that surface chemistry may impact the orientation of the nanotubes towards the glomerula capillary pores thus promoting renal clearance despite the high molecular weight. Ruggiero et al., Proc Natl Acad Sci USA 107(27), 12369-12374 (2010).

The data indicate MPS versus renal clearance in the case of PVX; however, a combination of clearance mechanisms may play a role. Based on the small dimensions along the short axis, renal clearance of PVX cannot be ruled out. Alternatively, it is also possible that digested or broken PVX fragments are routed through the kidneys. Nevertheless, it is indicated that the majority of the injected dose underwent hepatobiliary processing followed by excretion into the bile and feces. This is consistent with the behavior of elongated mesoporous silica nanoparticles and single-walled carbon nanotubes (SWNTs). Choi et al., Nat Biotechnol 25(10), 1165-1170 (2007). These hard, inorganic materials are secreted into the bile slowly, e.g. it took 2 months for SWNTs to be cleared from mice by hepatobiliary and renal processing. In contrast, it was found that PVX was cleared within a few days (FIG. 6).

To summarize, PVX is cleared from circulation by the MPS and accumulates in spleen and liver; the majority of PVX filaments are cleared via hepatobiliary route, while a smaller amount is processed through renal clearance.

Liver and spleen immunofluorescence following the administration PVX. Nanoparticles tend to be sequestered rapidly by dendritic cells, blood monocytes and tissue-resident macrophages in the liver, spleen, and lymph nodes, which are responsible for clearing, processing and degrading foreign materials from circulation. Owens D E, 3rd, Peppas N A, Int J Pharm 307(1), 93-102 (2006). The association of PVX with resident macrophages in the liver and spleen was evaluated by preparing cryosections of these tissues from mice injected with A647-PVX-PEG or with PBS as a control, and staining them with DAPI and antibodies for the detection of CD31 (endothelial cells) and F4/80, which is expressed in a range of macrophages irrespective of lineage. Sadauskas et al., Part Fibre Toxicol 4, 10 (2007).

Confocal microscopy was used to colocalize PVX (labeled directly with A647) and macrophages stained with anti-F4/80 (detected with a secondary antibody conjugated to A555). Strong PVX signals were detected in the liver and spleen at 24 and 72 h post-injection, and these were colocalized with the A555 signal in the liver, whereas in the spleen the signals remained separate. Mander's colocalization coefficients (M2 values) were determined using ImageJ resulting in values of 0.351 and 0.913 for the liver at 24 and 72 h, respectively, probably reflecting the uptake of PVX by Kupffer cells. Colocalization with endothelial cells stained with an antibody against CD31 showed the opposite trend, with M2 values falling from 0.976 to 0.379 between 24 and 72 h. In the spleen, PVX did not colocalize significantly with either CD31 or F4/80. The relative positions of F4/80 and PVX staining in the spleen indicate that PVX filaments are sequestered into the white pulp, surrounded by the red pulp which comprises F4/80-positive macrophages.

The spleen is a secondary lymphoid organ with a central role in primary defense against all types of antigens that appear in the circulation, and it is a major site of antibody production. Nanoparticles may be taken up by a variety of immune cells in the bloodstream and in tissues. To gain further insights into the tissue distribution of PVX within the spleen, composite images of entire spleens were generated using a Zeiss Axio Observer Z1 FL inverted microscope fitted with a motorized stage. It was found that PVX filaments were clustered, and accumulated in the white pulp regions of the spleen. Fluorescence and confocal imaging were used to study the colocalization of PVX with B-cell follicles using B220 as a marker (Cho et al., Nat Nanotechnol 6(10), 675-682 (2011)), with T-cells using CD3 as a marker (Dinauer et al., Biomaterials 26(29), 5898-5906 (2005)), and with activated T-cells using CD223 as a marker (Richter et al., Int Immunol 22(1), 13-23 (2010)). A647-PVX-PEG appeared to colocalize with $B220^+$ B-cells in the white pulp supported by M2 values of 0.866 and 0.762 at 24 and 72 h post-injection, respectively. Although there was no apparent colocalization with CD223 or CD3, there was a significant increase in $CD223^+$ cells 72 h post-injection compared to the 24 h time point.

The accumulation of PVX filaments in B-cells combined with the higher number of T-cells in the spleen may indicate that the PVX particles are immunogenic. The sequestration of PVX into $B220^+$ B-cells indicates the induction of a humoral immune response (reflecting the transport of antigens to B-cell follicles for germinal center reactions and affinity maturation) whereas the recruitment and activation of $CD223^+$ T-cells may also indicate the induction of a cellular immune response. This may imply that decoration of PVX with 380 PEG5000 chains is insufficient to achieve effective shielding and biocompatibility. This is an important observation because the development of VNPs thus far has focused on the use of low-molecular-weight PEG chains such as PEG500, PEG1000 and PEG2000. Steinmetz et al.: Small 7(12), 1664-1672 (2011); Steinmetz et al., Nano Lett 10(1), 305-312 (2010). Further research is therefore required to determine exactly how VNPs based on plant viruses interact with the immune system and whether shielding chemistries such as PEGylation are sufficient to prevent immunogenicity.

To summarize, immunofluorescence imaging indicates that PVX is taken up by the resident macrophages (e.g. Kupffer cells) in the liver. In the spleen, PVX is localized in the B-cell follicle-rich white pulp and promotes significant increase in the CD223+ T-cells at 72 hours post administration, which may indicate immunogenic properties of PVX. Nevertheless, further research has indicated that PEGylation is indeed an effective strategy to avoid innate immunity (see discussion and examples below).

Figure 7:
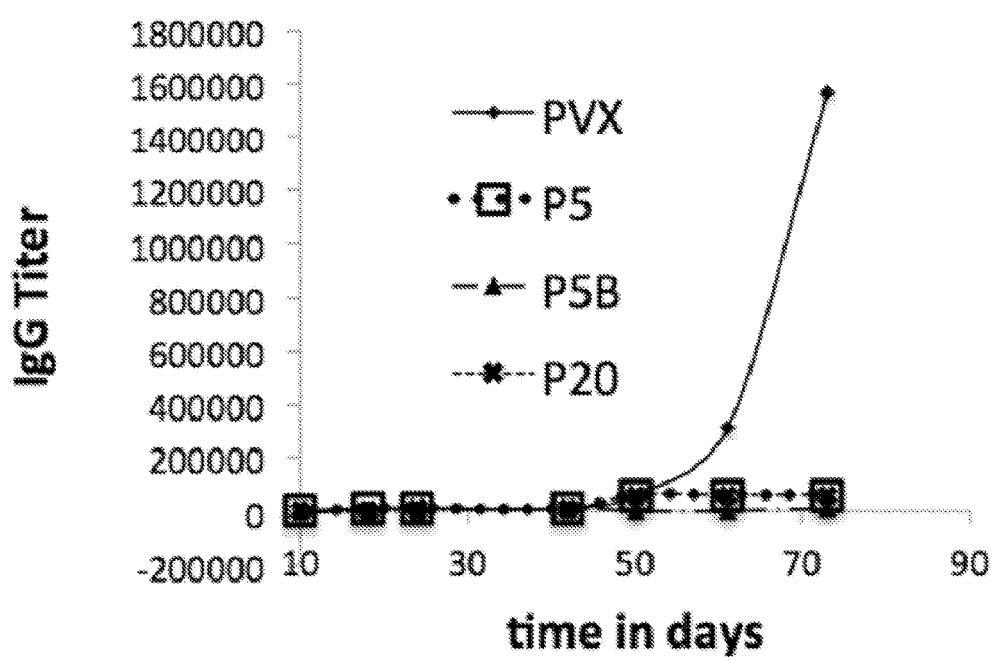
FIG. 7 provides a graph showing the results of an evaluation of whether clearance is associated with the development of a humoral immune response using native and PEGylated PVX in Balb/c mice. The results show that native PVX is immunogenic and a humoral immune response is apparent, while PEGylated PVX is effectively shielded from induction of PVX neutralizing antibodies.

Previous biodistribution data indicate clearance of PVX through the MPS system with accumulation in liver and spleen. To test whether clearance is associated with the development of a humoral immune response, native and PEGylated PVX was evaluated in Balb/c mice. A chemotherapy schedule was mimicked and PVX, PVX-P5 (conjugated with linear PEG of a molecular weight of 5,000 Da), and PVX-P5B (conjugated with branched PEG of a molecular weight of 5,000 Da), and PVX-P20 (conjugated with linear PEG of a molecular weight of 20,000 Da) at 100 micrograms were administered intravenously at days 0, 5, and 10. An additional booster was administered at day 42. IgG titers were measured using standard ELISA protocols. The results are shown in FIG. 7. Data indicate that native PVX is immunogenic and a humoral immune response is apparent. In stark contrast, PEGylated PVX appears to be effectively shielded from induction of PVX neutralizing antibodies. This result further supports the development of PVX as a medical cargo delivery system.

PVX-tumor homing studies in preclinical mouse models: The inventors have previously shown that elongated PVX filaments achieve strong tumor homing and accumulation in a mouse tumor model of colon cancer and a chicken chorioallantoic membrane (CAM) model of squamous carcinoma and fibrosarcoma. This may be consistent with the tumor-homing properties of other filamentous nanoparticles, e.g. filomicelles. Christian et al., Mol Pharm 6(5), 1343-1352 (2009); Moghimi et al., Annu Rev Pharmacol Toxicol 52, 481-503 (2012). Here, PVX-tumor homing was investigated in a set of mouse tumor models representing colon, brain and breast cancer.

Figure 8:
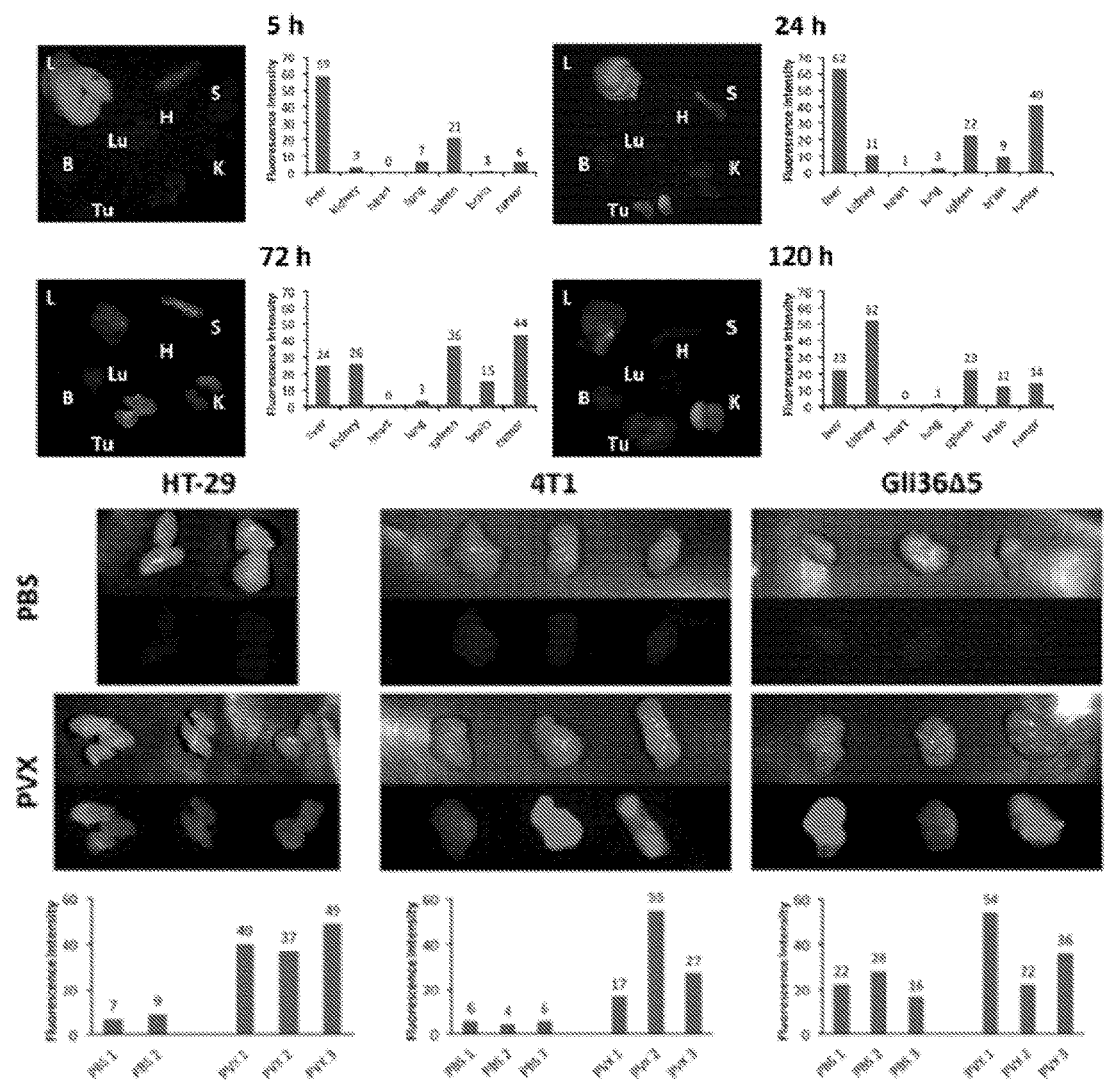

Time course studies were conducted over a 5-day time frame using a HT-29 (colon cancer) NCr nu/nu mouse tumor s.c xenograft model. A single dose of A647-PVX-PEG (10 mg/kg body weight) was injected into the tail vein (n=3) and tissues were collected for analysis using Maestro ex vivo imaging, immunofluorescence staining and confocal microscopy after 5, 24, 72 and 120 h (FIG. 8). Tumor homing was not evident after 5 h but strong fluorescence signals were observed at the 24 h time point indicating the strong homing of PVX to HT-29 tumors. At 24-72 h PVX tumor accumulation peaked accounting for 30% of the injected dose; the remaining particles appeared sequestered in liver and spleen reflecting MPS clearance (as discussed above). Fluorescence in the tumor and in the liver dropped significantly after 5 d as the PVX particles were cleared. Strong signals from the kidneys indicated the degradation of PVX followed by renal filtration en route to the bladder (FIG. 8B). This also is consistent with findings from healthy BALB/c mice where clearance through the bile and urine is indicated.

Particularly interesting is the fact that the observed fluorescence from the tumors at 5 h is significantly lower compared to liver and spleen. At later time points, 24-72 h post administration, tumor homing increases significant accounting for 30% of the injected PVX dose. This is interesting, because PVX has a plasma circulation half-life of only 12.5 min Tumor homing solely based on enhanced permeability and retention effects is thus unlikely. Data indicate that another mechanism plays a role in tumor homing and transport. The potential exists that tumor accumulation could be mediated by the phagocytosis of PVX followed by migration of the phagocytes into tumors. Similar mechanisms have been proposed for inorganic nanoparticles. Toraya-Brown et al., Integrative biology: quantitative biosciences from nano to macro 5(1), 159-171 (2012) Immunofluorescence data indicate that PVX filaments accumulated close to the endothelium (stained with an antibody specific for CD31), but were not colocalized or confined within the endothelium. Tumor sections were stained for macrophage markers, but there was no evidence of co-localization of PVX with the markers studied. Future studies must be carried out to elucidate on the tumor homing mechanism of PVX and to identify its intra-tumoral localization.

The tumor homing characteristics of PVX were also tested using two other preclinical mouse models, an ectopic Gli36Δ5 brain tumor xenograft in NCr nu/nu mice and an orthotopic 4T1 mammary tumor xenograft in the mammalian glands of female BALB/c mice. A647-PVX-PEG was injected into the tail vein of both models, and tumors were harvested along with other tissues from sacrificed mice after 24 h. Maestro imaging confirmed tumor homing in both the 4T1 and Gli36Δ5 xenografts, which showed significantly higher fluorescence signal intensity compared to tumors from control mice injected with PBS.

PVX tumor homing was observed in all three tumor models, but the fluorescence signals compared to the PBS controls were generally stronger in the HT-29 model than the others. The uptake of VNPs by tumors depends on many physiological parameters including vascular and collagen density which affect interstitial pressure and hence extravasation. Torosean et al., Nanomedicine, 9, 151-8 (2013). Furthermore, secondary mechanisms of PVX-tumor homing must be considered; parameters influencing tumor accumulation could be related to the degree of macrophage infiltration and other immune-regulatory characteristics. CD31 staining suggested that HT29 and 4T1 tumors were more vascularized than Gli36Δ5 tumors. Furthermore, based on the colocalization coefficients, PVX appears to be relatively more associated with the vasculature (CD31) in Gli36Δ5 tumors than the other models. This could also indicate that PVX extravasates less efficiently from the Gli36Δ5 tumor vasculature into the tumor, and thus accumulates to a lower level. Sections form each tumor were stained for B cell marker (B220) and macrophage markers (F4/80) in order to observe any association of PVX with these cell types within the tumor microenvironment. However, significant co-localization of PVX with either of the cell populations within tumors was not observed.

To summarize, up to 30% of the injected PVX dose is retained tumor tissue for several days. PVX shows tumor homing in several different tumor xenograft mouse models including colon cancer, brain cancer and breast cancer models. Gradual buildup of PVX in tumors days past its circulation half-life suggests a secondary mechanism of tumor homing (in addition or instead of enhanced permeability and retention effect).

Conclusions

In conclusion, biodistribution and physiological fate of PVX-based nanoparticles is described; a set of healthy mice and mouse models of human tumors were studied over a 5-day time course. Biodistribution and clearance studies suggest that PVX is sequestered in MPS organs spleen and liver; clearance occurs after several days through the hepatobiliary system and to a smaller degree via renal clearance.

In the liver, PVX co-localizes with F4/80-positive macrophages, likely Kupffer cells. Sadauskas et al., Part Fibre Toxicol 4, 10 (2007). In the spleen, PVX filaments were localized within the white pulp; specifically B-cell follicles. The accumulation of PVX within B-cells may indicate intrinsic immunogenicity (however, production of anti-PVX antibodies was shown to be significantly reduced). Besides all the advantages of VNPs, such as ease of production, reproducible genetic and chemical modification, monodisperse structures, various shapes and sizes are naturally available, stability under various bathing conditions, a potential hurdle toward clinical translation of these protein-based carrier systems is that the repetitive coat proteins can induce an immune response and thus hamper biocompatibility; optimization of the PEG coating and measurement of IgG titers must therefore be included in preclinical testing, when developing a PVX-based product for clinical translation.

It has been generally accepted that PEGylation is a reliable strategy to overcome immunogenicity. Steinmetz N F, Manchester M, Biomacromolecules 10(4), 784-792 (2009). Nevertheless, effectiveness of "stealth" effect and avoidance of immune surveillance must be carefully evaluated. Variables to test are the PEGylation density, confirmation, and attachment sites. Research on VNPs has focused on the application of low-molecular-weight PEG chains such as PEG500, PEG1000 and PEG2000. As described herein, the effects of branched and linear PEG 5,000 and PEG 20,000 have now been evaluated.

The PEG conformation (brush versus mushroom) on the nanoparticle surface is a key parameter that influences biodistribution and clearance. Overall, the more PEG chains attached and the more densely packed they are (favoring the brush conformation), the more effectively the formulation is shielded. Perry et al., Nano Lett, 12, 5304-10 (2012). The PEG conformation depends on the grafting density and Flory radius ($R_F=aN^{3/5}$ where a is the persistence length of the PEG monomer (a=0.35 nm) and N is the number of PEG monomers). If the grafting density is less than the Flory radius, the PEG chains adopt a mushroom conformation, whereas grafting densities higher than the Flory radius result in an extended brush conformation. Given that ~380 PEG chains are attached to the PVX particles taking into account their surface area of the 515 nm by 13 nm cylinder, it was calculated that one PEG5000 chain is attached on average every 56 nm along the filament. The Flory dimension of PEG5000 is ~6 nm, which suggests the PEG chains adopt a mushroom conformation on the PVX surface. To achieve PEGylation with PEG chains being presented in brush confirmation; labeling efficiency must be significantly increased; for example conjugation of ~600 PEG chains with a molecular weights of 20,000 Da, transition to brush confirmation might occur. Indeed, the inventors confirmed effective shielding from the immune response using PEG 5,000 linear and branched as well as PEG 20,000. The circulation time increases 10-fold upon conjugation of PEG 20,000 vs PEG 5,000. Most effective immune response suppression was achieved using PEG 5,000 branched.

Profound tumor homing with titers reaching up to 30% of the injected dose of PVX accumulating in the tumor tissue was observed. A647-PVX-PEG5000, used in this study, has a short plasma circulation time of $t_{1/2}=12.5$ min. It was therefore interesting to observe that tumor homing significantly increases after 24-72 h post administration compared to the 5 h time point. Clearance from the blood pool within minutes is thus not consistent with tumor homing via the enhanced permeability and retention effect. The inventors hypothesize that other mechanisms lead to the delayed tumor accumulation of PVX. It is possible that tumor-associated macrophages or other types of immune cells take up PVX and transport the nanoparticle formulation into the tumor tissue Immunofluorescence data indicate localization of PVX in near proximity of the endothelium; however, the intra-tumoral localization of PVX is yet to be identified. Mechanistic studies must be carried out to identify the cell types PVX associates with; this is important for further tailoring of PVX as a cargo-delivery vehicle.

PVX is potentially an interesting platform for drug delivery and imaging because of its large surface area and corresponding high payload capacity, its biodegradability, and its efficient tumor homing properties. The discipline of plant-based VNP technology in drug delivery is still an emerging discipline, only a few VNP-based materials have undergone in vivo testing. Understanding biodistribution and clearance is the first step toward tailoring a particular of the VNP platform for potential clinical applications.

With a significantly improved understanding of nanoparticles clearance mechanisms and biological fates, several novel nanoparticle platforms will be able to make the first crucial transition from preclinical to clinical studies. Majority of these platforms will be based on biodegradable materials that will carry payloads of therapeutic molecules and contrast agents for therapeutic or imaging applications. Inclusion of targeting ligands in the formulations will result in a largely tissue-targeted accumulation of the nanoparticle carriers with minimum non-specific accumulations. Also, with the development of improved surface passivation strategies such as camouflage with self peptides or different stealth polymers, e.g. zwitter ionic polymers, in conjugation with the evolving shapes, prolonged circulation of nanocarriers will materialize resulting in availability of sustained dosages of therapeutic molecules and necessity for fewer repetitive administrations. These factors together are expected to improve outcomes of nanomaterial-based therapeutic strategies with reduced toxicity and adverse effects.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. A method of targeting cancer tissue in a subject, comprising administering to the subject a Potato virus X species carrier comprising a Potato virus X species virus particle modified to carry an imaging agent or a cytotoxic compound, wherein the Potato virus X species carrier has been PEGylated such that the grafting density of PEG chains on the virus particles surfaces is higher than the Flory radius of the PEG chains, wherein the Potato virus X species carrier has been PEGylated with PEG having a molecular weight greater than or equal to about 5000 daltons.

2. The method of claim 1, wherein the Potato virus X species carrier comprises an imaging agent.

3. The method of claim 2, wherein the imaging agent is a fluorescent molecule for fluorescent imaging.

4. The method of claim 2, wherein an effective amount of a Potato virus X species carrier is administered, and further comprising the step of imaging cancer tissue in the subject using an imaging device subsequent to administering the Potato virus X species carrier.

5. The method of claim 1, wherein the Potato virus X species particle comprises a cytotoxic compound.

6. The method of claim 5, wherein the cytotoxic compound is an antitumor agent.

7. The method of claim 1, wherein the cancer tissue is colon cancer, brain cancer, breast cancer, fibrosarcoma, or squamous carcinoma.

8. A method of treating cancer in a subject identified as having cancer by administering to the subject a therapeutically effective amount of a Potato virus X species carrier comprising a Potato virus X species particle modified to carry a cytotoxic compound, wherein the Potato virus X species carrier has been PEGylated such that the grafting density of PEG chains on the virus particles surface is higher than the Flory radius of the PEG chains, wherein the Potato virus X species carrier has been PEGylated with PEG having a molecular weight greater than or equal to about 5000 daltons.

9. The method of claim 8, wherein the cytotoxic compound is an antitumor agent.

10. The method of claim 7, wherein the cancer is colon cancer, brain cancer, or breast cancer.

11. The method of claim 7, wherein the Potato virus X species carrier is administered together with a pharmaceutically acceptable carrier.

12. A Potato virus X species carrier, comprising a Potato virus X species particle that has been modified to carry an imaging agent or cytotoxic compound, wherein the Potato virus X species carrier has been PEGylated such that the grafting density of PEG chains on the virus particles surface is higher than the Flory radius of the PEG chains, wherein the Potato virus X species carrier has been PEGylated with PEG having a molecular weight greater than or equal to about 5000 daltons.

13. The method of claim 1, wherein the imaging agent is a near infrared fluorophore.

14. The method of claim 13, wherein the near infrared fluorophore is A647.

15. The method of claim 12, wherein the fluorescent molecule for fluorescent imaging is a near infrared fluorophore.

16. The method of claim 15, wherein the near infrared fluorophore is A647.

* * * * *